United States Patent [19]

Mooberry et al.

[11] 4,358,525
[45] Nov. 9, 1982

[54] BLOCKED PHOTOGRAPHICALLY USEFUL COMPOUNDS AND PHOTOGRAPHIC COMPOSITIONS, ELEMENTS AND PROCESSES EMPLOYING THEM

[75] Inventors: Jared B. Mooberry; William C. Archie, Jr., both of Rochester, N.Y.

[73] Assignee: Eastman Kodak Company, Rochester, N.Y.

[21] Appl. No.: 292,095

[22] Filed: Aug. 12, 1981

Related U.S. Application Data

[63] Continuation-in-part of Ser. No. 949,462, Oct. 10, 1978, Pat. No. 4,310,612.

[51] Int. Cl.$^3$ ............... G03C 1/40; G03C 1/48; G03C 5/54; G03C 1/10
[52] U.S. Cl. .................. 430/217; 430/212; 430/218; 430/219; 430/222; 430/223; 430/543; 430/544; 430/559; 430/562; 430/564; 430/566; 430/570; 430/598; 430/955; 430/957; 430/959; 430/960

[58] Field of Search ............ 430/218, 219, 217, 212, 430/222, 223, 224, 226, 955, 956, 958, 959, 960, 559, 566, 564, 598, 543, 544, 570, 563, 562, 957

[56] References Cited

U.S. PATENT DOCUMENTS

| | | | |
|---|---|---|---|
| 3,980,479 | 9/1976 | Fields | 430/219 |
| 4,199,354 | 4/1980 | Hinshaw et al. | 430/219 |
| 4,310,612 | 1/1982 | Mooberry et al. | 430/563 |

Primary Examiner—Richard C. Schilling
Attorney, Agent, or Firm—Joshua G. Levitt

[57] ABSTRACT

Photographically useful compounds such as photographic reagents and photographic dyes are blocked with a grouping which, under alkaline conditions, is cleaved from the compound by an intramolecular nucleophilic displacement reaction. The compounds are resistant to unblocking under storage conditions, but are uniformly unblocked under conditions encountered during photographic processing.

28 Claims, No Drawings

BLOCKED PHOTOGRAPHICALLY USEFUL COMPOUNDS AND PHOTOGRAPHIC COMPOSITIONS, ELEMENTS AND PROCESSES EMPLOYING THEM

This is a continuation-in-part of U.S. patent application Ser. No. 949,462 filed Oct. 10, 1978, now U.S. Pat. No. 4,310,612.

This invention relates to blocked photographically useful compounds such as photographic image dyes, and photographic reagents; to photographic compositions and elements containing such blocked photographically useful compounds; and to processes for preparing images with such compositions and elements. In particular, this invention relates to such compounds, compositions, elements and processes wherein the compound is blocked by a group which is resistant to cleavage during storage but which is uniformly cleavable under conditions of processing.

Preformed image dyes are contained in photographic elements intended for use with various photographic processes. An image can be formed with such elements by a change in the dye resulting from exposure of the element. For example, in various color diffusion transfer processes an image-wise change in mobility of a dye is effected as a function of silver halide development. As another example, in the silver dye bleach process (described in Mees and James, *The Theory of the Photographic Process*, pages 394 and 395, Third Edition, 1966, The MacMillan Company, New York; and in Meyer, *The Journal of Photographic Science*, Vol. 13, 1965, pages 90–97), a uniform distribution of dye is destroyed imagewise as a function of silver halide development.

In such processes the dye is not acted upon directly by exposing radiation, but responds to a change resulting from development of an exposed photosensitive material, such as silver halide. When the image is to be formed by the subtractive technique of color formation, the image dyes generally absorb radiation in the region of the spectrum to which the associated silver halide is sensitive. Thus, a yellow dye is associated with blue-sensitive silver halide, a magenta dye is associated with green-sensitive silver halide and a cyan dye is associated with red-sensitive silver halide.

If in such an element the dye and the silver halide are incorporated in the same layer, the dye will act as an unwanted filter, absorbing a portion of the exposing radiation which otherwise would reach the silver halide. This results in a loss in sensitivity (photographic speed).

One way to eliminate this unwanted filtering effect is to have the silver halide and the dye in separate layers of the element, while maintaining them in reactive association. By locating the dye further from the source of exposure than the silver halide, the dye is unable to filter exposing radiation before it reaches the silver halide. While this is a useful and practical solution, it increases the number of layers in the photographic element, resulting in a thicker element which, inter alia, takes longer to yield a viewable image than if the dye and silver halide were in the same layer.

Another way of eliminating the filtering effect of image dyes is to reversibly shift the spectral absorption of the image dye to shorter wavelengths (hypsochromically) or to longer wavelengths (bathochromically). After exposure, typically during processing, the spectral absorption of the dye is reshifted to return the dye to the desired color. This has been accomplished by attaching to the dye molecule a blocking group, i.e., a group which causes a shift in the spectral absorption of the dye but which is cleavable from the dye during or after processing.

To understand the way in which a blocking group functions in shifting the spectral absorption of a dye, it is necessary to understand the reason dyes are colored. Color in dyes is attributed to absorption of electromagnetic radiation by a conjugated system of single and double bonds in the dye molecule, commonly referred to as a chromophoric system. The chromophoric system is generally terminated with an electron donating group, such as a hydroxy group, a mercapto group or an amino group, which extends the conjugation of the chromophoric system and intensifies the color of the dye. These electron donating groups are referred to as auxochromes. A blocking group is typically an electron withdrawing group, such as an acyl group, and is joined to the auxochrome so as to modify the availability of electrons in the conjugated system and thereby change the spectral absorption characteristics of the dye.

Shifting of photographic image dyes by blocking an auxochromic group of the dye is further discussed in U.S. Pat. Nos. 3,230,085; 3,307,947 and 3,579,334 (which relate to shifting of image dyes intended for use in diffusion transfer elements and processes) and in U.S. Pat. No. 3,684,513 (which relates to shifting of image dyes intended for use in silver dye bleach elements and processes). The dyes described in these patents are shifted in such a way that the bond between the blocking group and the auxochrome is cleaved by hydrolysis, or an analogous reaction, during or after photographic processing.

One difficulty with this approach to eliminating the filtering effect of image dyes is that it requires a compromise between two essentially antithetical requirements; i.e., good storage stability of the dye in the shifted, blocked form, and rapid removal of the blocking group with reshifting of the dye, during processing. Thus, this approach heretofore has resulted in dyes that either had good storage stability but became unblocked at an unduly slow rate during processing, or dyes that became unblocked at a desirably rapid rate during processing, but which had poor storage stability due to premature hydrolysis.

Thus, there has been a need for shifted photographic image dyes which are blocked in such a way that the shifted form of the dye is stable during storage yet rapidly unblocks during processing to reshift the dye to the desired color.

We have found shifted photographic dyes which satisfy this need. Our dyes contain a blocking group which, under alkaline conditions such as exist during photographic processing, is uniformly cleaved from the dye as a result of an intramolecular nucleophilic displacement reaction within the blocking group.

The term "intramolecular nucleophilic displacement reaction" is understood to refer to a reaction in which a nucleophilic center of a compound reacts directly, or indirectly through an intervening molecule, at another site on the compound, which is an electrophilic center, to effect displacement of a group or atom attached to the electrophilic center. Generally, such a compound has a nucleophilic group and an electrophilic group spatially related by the configuration of the molecule to promote reactivity. Preferably the nucleophilic group and the electrophilic group are located in the compound so that a cyclic organic ring, or a transient cyclic organic ring, can be easily formed during the intramolecular reaction involving the nucleophilic center and the electrophilic center. A nucleophilic group is understood to be a grouping of atoms one of which has a relatively high electron density. This atom is referred to as the nucleophilic center. An electrophilic group is understood to be a grouping of atoms one of which has a relatively low electron density. This atom is referred to as the electrophilic center.

By employing dyes in which the blocking group is cleaved as a result of an intramolecular nucleophilic displacement reaction, the need to compromise between good storage stability and rapid unblocking of the dye is avoided. With such dyes the linkage between the blocking group and the auxochromic group is resistant to cleavage (e.g. by hydrolysis) under storage conditions, yet rapid unblocking of the dye is obtained under alkaline processing conditions as a result of cleavage of this storage-stable linkage by an intramolecular nucleophilic displacement reaction.

As in the case of photographic image dyes, there are frequently incorporated in photographic elements photographic reagents such as development inhibitors, development accelerators, developing agents, electron transfer agents, dye-forming couplers, competing couplers, DIR couplers and compounds, silver halide solvents, silver complexing agents, fixing agents, toners, hardeners, fogging agents, antifoggants, chemical sensitizers, spectral sensitizers, desensitizers, and the like. It is often desirable that these reagents be blocked prior to processing so as to prevent premature reaction of the reagent during storage. The blocking technology of this invention, described above in connection with photographic image dyes, can be usefully employed to block or immobilize a photographic reagent. The blocking group can be attached on an atom of the photographic reagent, e.g., a sulfur, nitrogen, oxygen, selenium or phosphorous atom, which is responsible for the reactivity of the photographic reagent. Blocking will then inactivate the reagent until the blocking group is cleaved during processing. Similarly, if the atom to which the blocking group is attached is in conjugation with a group which is responsible for the reactivity of the photographic reagent, blocking can inactivate the reactive group by modifying the electron distribution within the molecule. If the atom to which the blocking group is attached is not of either of these types, the blocking group can be ballasted and thereby provide sufficient bulk to immobilize the photographic reagent at a location removed from where it is to be ultimately used. In each of these cases, the blocking group is uniformly cleaved from the photographic reagent during processing thereby converting the photographic reagent to its active and mobile form. As in the case of photographic image dyes, the blocking group can be selected to rapidly cleave upon commencement of photographic processing. However, in some circumstances it may be desirable to delay the availability of the photographic reagent until processing has proceeded to some extent, or even until processing has been substantially completed. In this case, the blocking group can contain substituents which will retard cleavage from the photographic reagent. Thus the present invention provides blocked photographic reagents which are stable under storage conditions but which can be uniformly cleaved under processing conditions in a controlled manner.

Compounds which can undergo an intramolecular nucleophilic displacement reaction have been employed previously in the photographic art, particularly in elements intended for use in diffusion transfer processes. They are described in, for example, Hinshaw et al U.K. Patents 1,464,104 and 1,464,105, Fields et al U.S. Pat. No. 3,980,479 and Chasman et al U.S. Pat. No. 4,139,379. These compounds undergo an intramolecular nucleophilic displacement reaction in connection with release of a diffusible dye, or another photographically useful compound, from a carrier as a function of silver halide development and a related oxidation or reduction reaction. Hence in these compounds the intramolecular nucleophilic displacement reaction (1) is affected by silver halide development, (2) occurs in an imagewise manner and (3) effects a change in the mobility of the dye or other photographically useful compound.

In the dyes of the present invention, cleavage of the blocking group (1) is not affected by silver halide development, (2) occurs uniformly under conditions of processing, and (3) does not significantly change the mobility of the dye although the dye may contain another moiety, such as a carrier, which will be responsible for an imagewise change in mobility of the dye as a function of silver halide development.

In the photographic reagents of the present invention, cleavage of the blocking group (1) is not affected by silver halide development, (2) occurs uniformly under conditions of processing but (3) may change the mobility of the photographic reagent.

In accordance with one aspect of this invention there is provided a photographic image dye in which there is joined to an auxochromic group of the dye, a blocking group which shifts the spectral absorption of the dye, the blocking group being a group which, under alkaline conditions, is uniformly cleavable from the dye by an intramolecular nucleophilic displacement reaction within the blocking group without changing the mobility of the dye.

In accordance with another aspect of this invention there is provided a photographic reagent containing a blocking group which, under alkaline conditions, is uniformly cleavable from the reagent by an intramolecular nucleophilic displacement reaction within the blocking group.

One embodiment of this invention is a shifted photographic image dye as described above. Included in this embodiment are photographic image dye-providing compounds in which the dye further includes a moiety which under alkaline conditions and as a function of silver halide development (direct or inverse) changes the mobility of the dye.

Another embodiment of this invention is a blocked photographic reagent as described above.

A further embodiment of this invention is a photographic element comprising a support bearing at least one layer of a shifted photographic image dye and/or a blocked photographic reagent as described above. Included in this embodiment are silver halide photographic elements and color diffusion transfer elements.

A still further embodiment of this invention is a photographic silver halide emulsion containing shifted photographic image dyes and/or blocked photographic reagents as described above.

A yet further embodiment of this invention is a process of preparing photographic images with the above dyes, reagents, emulsions or elements.

Dyes of this invention can be represented by the structure:

DYE—G—INDR    I wherein:

DYE-G is the residue of a photographic image dye, G being the residue of an auxochromic group of the dye; and INDR is a blocking group which shifts the spectral absorption of the dye and which, under alkaline conditions, is uniformly cleavable from G by an intramolecular nucleophilic displacement reaction within INDR, without changing the mobility of the dye.

The moiety represented by DYE-G can be the residue of any dye which is usefully incorporated in a photographic element to provide a photographic image, so long as the dye contains an auxochromic group available for derivitization with a blocking group. Representative auxochromic groups contained in photographic image dyes are hydroxy, mercapto and amino groups. With such auxochromes, G in the above formula would be, respectively, oxygen, sulfur and amino. Useful photographic image dyes include azo aromatic dyes (such as azophenols, azonaphthols, azoindoles, azopyridinols, azopyrimidols, azopyrazoles, azopyrazolotriazoles, azoisoquinolinols, arylazovinylols, azoanilines and azothiophenols) and azomethine dyes (such as indophenols, indonaphthols, indamines and indoanilines). Preferred image dyes are indoaniline dyes and hydroxyaromatic dyes (such as azophenols, azonaphthols, azopyridinols and indophenols.)

The blocking group represented by INDR, is a group which is resistant to cleavage from G under storage conditions, but which under alkaline conditions, such as exist during photographic processing, is rapidly and uniformly cleavable from G by an intramolecular nucleophilic displacement reaction. It can contain an electrophilic group directly attached to G by a hydrolysis resistant bond and a hydrolysis sensitive precursor of a nucleophilic group spatially related with the electrophilic group so that upon generation of the nucleophilic group under alkaline conditions, the electrophilic group and the nucleophilic group undergo an intramolecular nucleophilic displacement reaction to cleave the blocking group from the auxochromic group of the dye.

The blocking group is selected so that cleavage from the dye, or dye providing compound, may have a minor effect on the mobility of the dye, e.g., making it slightly more mobile or slightly less mobile, but does not have a significant effect on mobility, i.e., changing an otherwise immobile compound to a mobile compound, or vice versa.

Photographic reagents of this invention can be represented by the structure:

PR—G'—INDR    II wherein:

PR—G' is the residue of a photographic reagent, G' being oxygen, sulfur, selenium, phosphorous or nitrogen attached to or contained in the photographic reagent; and INDR is a blocking group as described above which, under alkaline conditions, is uniformly cleavable from G' by an intramolecular nucleophilic displacement reaction within INDR.

Preferred classes of dyes and photographic reagents of this invention can be represented by the structures:

DYE—G—E—X—NuP    III

PR—G'—E—X—NuP    IV wherein:

DYE—G is as defined above;

PR—G' is as defined above;

E is an electrophilic group;

NuP is a precursor of a nucleophilic group which under alkaline conditions, is converted uniformly to a nucleophilic group and X is a linking group for spatially relating E and NuP to enable them to undergo, after conversion of NuP to a nucleophilic group, an intramolecular nucleophilic displacement reaction which cleaves the bond between E and G or G'.

The electrophilic group represented by E contains an atom of low electron density, such as $$\text{carbonyl } (-\overset{O}{\underset{\|}{C}}-), \text{ thiocarbonyl } (-\overset{S}{\underset{\|}{C}}-), \text{ sulfonyl } (-\overset{O}{\underset{\underset{O}{\|}}{\overset{\|}{S}}}-),$$

$$\text{phosphinyl } (-\overset{O}{\underset{\underset{O}{\|}}{\overset{\|}{P}}}-), \text{ or thiophosphinyl } (-\overset{S}{\underset{\underset{S}{\|}}{\overset{\|}{P}}}-),$$

as well as carbon doubly bonded to nitrogen ($>C=N-$) or carbon doubly bonded to carbon ($>C=C>$). Preferably, E forms a hydrolysis resistant bond with G such that the combination of E and G or E and G' represents an amide moiety or an ester moiety, such as a carboxy ester, a thiocarboxy ester, a carbamate ester, a sulfonate ester, a phosphinate ester. In a particularly preferred embodiment, the combination G—E or G'—E represents a carbamate ester or a sterically hindered carboxy ester. A sterically hindered carboxy ester is one in which the carbon atom of the carbonyl group is protected from external attack by a bulky group or groups on a neighboring atom.

The nucleophilic group precursor, NuP, preferably is a hydrolysis sensitive moiety which under alkaline conditions, such as exist during photographic processing, is converted to a nucleophilic group containing an oxygen, sulfur, nitrogen, phosphorus or carbon atom of high electron density. Preferably, the nucleophilic group precursor is a hydrolysis sensitive ester (including cyclic esters such as lactones) or amide (including cyclic amides such as imides).

The linking group, represented by X, provides the spatial relationship for the electrophilic group and the nucleophilic group to enter into an intramolecular nucleophilic displacement reaction. Such a reaction typically involves the formation of a 3- to 7-membered ring. Thus, in a preferred embodiment the electrophilic group and nucleophilic group precursor are joined to the linking group such that a 3- to 7-membered ring is formed during the intramolecular nucleophilic displacement. In a particularly preferred embodiment, a 5- or 6-membered ring is formed. In certain cases, portions of the electrophilic group and the nucleophilic group precursor can be considered to be part of the linking group. The linking group can be an acyclic, carbocyclic or heterocyclic moiety and can contain substituents which can serve various functions. These include modification of the rate of the intramolecular nucleophilic displacement reaction, enhancement of such properties of the photographic dye or reagent, before the blocking group is cleaved therefrom, as solubility, dispersability and nondiffusibility and enhancement of such properties of the blocking group, after it is cleaved from the dye, as mobility.

It will be appreciated that for an intramolecular nucleophilic displacement reaction to occur, breaking the bond between E and G or E and G', the thermodynamics should be such that the free energy of ring closure plus the bond energy of the bond formed between Nu and E is greater than the bond energy between E and G or E and G'. Not all possible combinations of G, G', E, X and NuP will yield a thermodynamic relationship favorable to breaking of the bond between E and G or E and G'. However, it is within the skill of the art to select appropriate combinations taking the above factors into account. These factors are discussed in more detail in Capon and McManus, *Neighboring Group Participation*, Volume 1, Plenum Press, New York, 1976.

The hydrolytic stability of the bond between G and the electrophilic groups contemplated for use in blocking groups and the hydrolytic sensitivity of nucleophilic group precursors contemplated for use in blocking groups can be determined by kinetic analysis of the rate at which the individual components of the blocking group hydrolyze in alkaline solution. A suitable technique is described in Jencks, *Catalysis In Chemistry And Enzymology*, pages 557–561, McGraw-Hill, 1969. Such an analysis will yield $t_{1/2}$ parameters, i.e., the time required for the hydrolysis reaction to be 50 percent completed. Such techniques can be applied to determine $t_{1/2}$ for the bond between G or G' and the electrophilic group and $t_{1/2}$ for the nucleophilic group precursor. For example, a dye can be blocked with an electrophilic group (without the nucleophilic group precursor) and the rate at which the bond between G and the electrophilic group is broken in alkali (e.g. 1 molar sodium hydroxide) can be determined by measuring (e.g. spectrophotometrically) the change in color of the dye at discrete intervals of time. Similarly, a nucleophilic group precursor can be attached to a simple compound and the conversion of the nucleophilic group precursor to a nucleophilic group in alkali can be measured at discrete intervals.

Such $t_{1/2}$ parameters will provide a guide in selecting hydrolysis resistant electrophilic groups and hydrolysis sensitive nucleophilic group precursors for use in the blocking groups. For the dyes and photographic reagents of this invention it is preferred that the hydrolysis resistant electrophilic group form a bond with G or G' (in formulae III or IV above) which, in the absence of the nucleophilic group precursor, has a $t_{1/2}$ for hydrolysis at pH 14 and ambient conditions of one thousand seconds or more, preferably a $t_{1/2}$ for hydrolysis of ten thousand to one million seconds. Additionally, for the dyes of this invention it is preferred that the hydrolysis sensitive nucleophilic group precursor have a $t_{1/2}$ for hydrolysis at pH 14 and ambient conditions of about one hundred seconds or less, preferably a $t_{1/2}$ for hydrolysis less than ten seconds. For the photographic reagents of this invention the hydrolysis sensitive nucleophilic group can have a $t_{1/2}$ for hydrolysis similar to that for the dyes if rapid unblocking on commencement of photographic processing is desired, or it can have a longer $t_{1/2}$ for hydrolysis if delay in unblocking is desired. When such an electrophilic group and such a nucleophilic group precursor are contained in a blocking group so as to be capable of entering into an intramolecular nucleophilic displacement reaction, the hydrolysis of the nucleophilic group precursor is the rate determining step, and hence provides enhancement of the rate of cleavage of the blocking group from the photographic dye or photographic reagent.

Representative blocking groups useful in this invention are listed below. In these groups the unsatisfied bond indicates the point of attachment to G or G' and the dashed line indicates the point at which the group that masks the nucleophilic group is cleaved to generate the nucleophilic group. Where more than one dashed line is shown, more than one point of cleavage is possible.

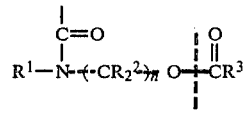

INDR-1 where:

$R^1$ is hydrogen, straight or branch chain alkyl of 1 to 20 carbon atoms (such as methyl, ethyl, isopropyl, butyl, t-butyl, pentyl, hexyl, octyl, etc.) or aryl of 6 to 30 carbon atoms (such as phenyl, chlorophenyl, nitrophenyl, methylphenyl, dioctylphenyl etc.);

$R^2$ is individually hydrogen or alkyl of 1 to 6 carbon atoms (such as methyl, ethyl, butyl, etc.);

$R^3$ is hydrogen, alkyl of 1 to 20 carbon atoms (such as methyl, fluoromethyl, trifluoromethyl, chloromethyl, dichloromethyl, trichloromethyl, ethyl, hexyl, cyclohexyl, octyl, dodecyl, methoxymethyl, phenoxymethyl, etc.) or aryl of 6 to 30 carbon atoms (such as phenyl, chlorophenyl, nitrophenyl, methylphenyl, dioctylphenyl, sulfamoylphenyl, sulfonamidophenyl, carbamoylphenyl, carbonamidophenyl, etc.); and n is 1 to 4.

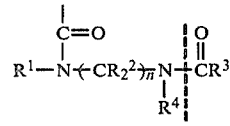

INDR-2 where:

n, $R^1$, $R^2$, and $R^3$ are as defined above and $R^4$ is $R^1$.

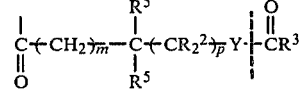

INDR-3 where:

Y is —O—, —S—, or

$R^2$, $R^3$ and $R^4$ are as defined above;

Each $R^5$ is individually straight or branch chain alkyl of 1 to 6 carbon atoms (such as methyl, ethyl, isopropyl, butyl, etc.);

m is 0 or 1;
p is 1 to 4; and
m+p is 1 to 4.

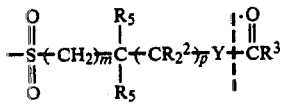

INDR-4 where:
m, p, Y, $R^2$, $R^3$, $R^4$ and $R^5$ are as defined above.

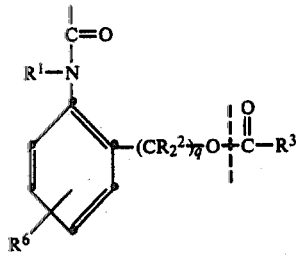

INDR-5 where:
$R^1$, $R^2$ and $R^3$ are as defined above;
q is 0 to 2; and
$R^6$ is hydrogen or one or more optional substituents such as halogen, nitro, carboxy, straight or branch chain alkyl of 1 to 20 carbon atoms; alkoxy of 1 to 20 carbon atoms, aryl of 6 to 30 carbon atoms, alkoxycarbonyl of 2 to 20 carbon atoms; sulfamoyl having the structure $-SO_2NR^4{}_2$, sulfonamido having the structure $-NR^4SO_2R^4$, carbamoyl having the structure $-CONR^4{}_2$ or carbonamido having the structure $-NR^4COR^4$ where $R^4$ is as defined above.

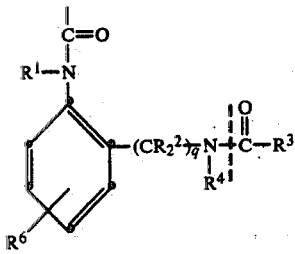

INDR-6 where:
q, $R^1$, $R^2$, $R^3$, $R^4$ and $R^6$ are as defined above.

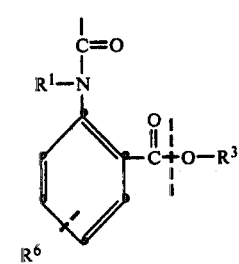

INDR-7 where:
$R^1$, $R^3$ and $R^6$ are as defined above.

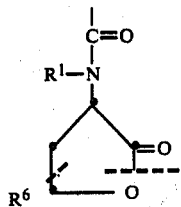

INDR-8 where:
$R^1$ and $R^6$ are as defined above.

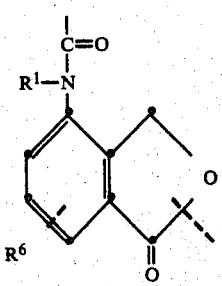

INDR-9 where:
$R^1$ and $R^6$ are as defined above.

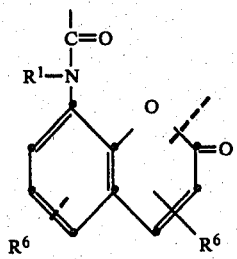

INDR-10 where:
$R^1$ and $R^6$ are as defined above.

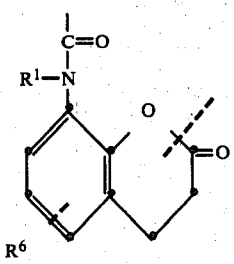

INDR-11 where:
$R^1$ and $R^6$ are as defined above.

INDR-12

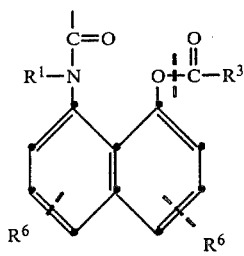

where:
R¹, R³, and R⁶ are as defined above.

INDR-13

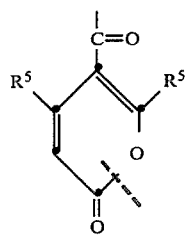

where:
R⁵ is as defined above.

INDR-14

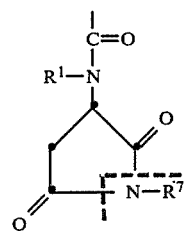

where:
R¹ is as defined above and
R⁷ is alkyl of 1 to 30 carbon atoms including substituted alkyl such as carboxyalkyl, alkoxycarbonylalkyl, sulfamoylalkyl, sulfonamidoalkyl, carbamoylalkyl, and carbonamidoalkyl, or aryl of 6 to 30 carbon atoms including substituted aryl such as alkaryl, sulfamoylaryl, sulfonamidoaryl, carbamoylaryl and carbonamidoaryl; the sulfamoyl, sulfonamido, carbamoyl and carbonamido moieties having the structure shown in connection with R⁶.

INDR-15

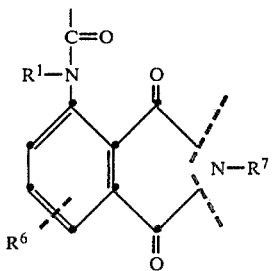

where:
R¹, R⁶ and R⁷ are as defined above.

INDR-16

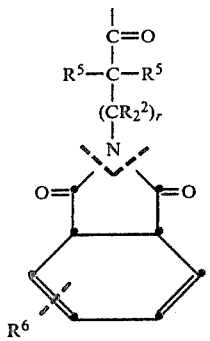

where:
R², R⁵ and R⁶ are as defined above and
r is 1 or 2.

INDR-17

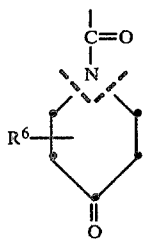

where:
R⁶ is as defined above.

INDR-18

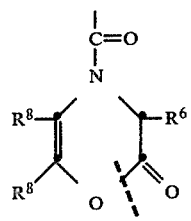

where:
R⁶ is as defined above and
Each R⁸ is R⁶ or together both R⁸'s form a fused aromatic ring of 5 to 6 nuclear atoms selected from carbon, nitrogen, oxygen and sulfur, which ring can be optionally substituted with one or more R⁶ groups.

INDR-19

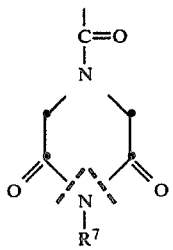

where:
R⁷ is as defined above.

INDR-20

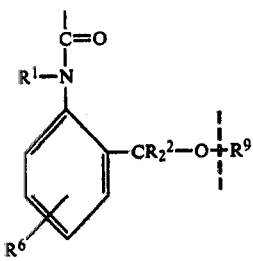

where:

$R^1$, $R^2$ and $R^6$ are as defined above; and $R^9$ is hydrogen, formyl, or alkylcarbonyl, of 2 to 30 carbon atoms especially substituted alkylcarbonyl such as haloalkylcarbonyl, alkoxyalkylcarbonyl, phenoxyalkylcarbonyl, aminoalkylcarbonyl and amidoalkylcarbonyl.

INDR-21

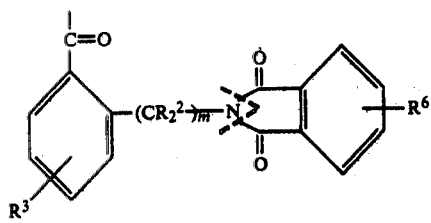

where:

m, $R^2$, $R^3$ and $R^6$ are as defined above.

INDR-22

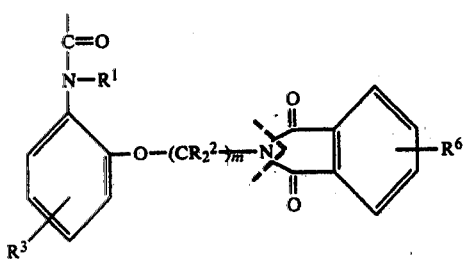

where:

m, $R^1$, $R^2$, $R^3$ and $R^6$ are as defined above.

INDR-23

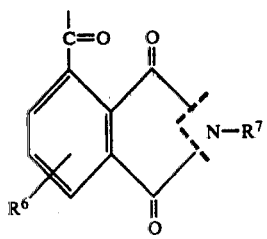

where:

$R^6$ and $R^7$ are as defined above.

INDR-24

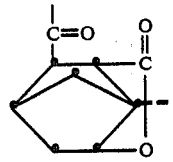

Especially preferred blocking groups are those having structures INDR-6, INDR-14 and INDR-15 where $R^1$ is alkyl of 1 to 4 carbon atoms, $R^2$ is hydrogen, q is 1, $R^3$ is trifluoromethyl, $R^4$ is alkyl of 1 to 4 carbon atoms, $R^6$ is hydrogen or $NHSO_2R^4$ and $R^7$ is alkyl of 1 to 4 carbon atoms.

The dye moiety to which the blocking group is attached can be any of the dye moieties useful in photographic elements to provide preformed image dyes. A preferred class of such dyes are azoaromatic dyes. Other useful image dyes are azomethine dyes including indophenol dyes and indoaniline dyes. Azoaromatic dyes are characterized by the moiety -N=N- attached to an aromatic ring, while azomethine dyes are characterized by a moiety -N=C< attached to an aromatic ring. A preferred subclass within these two classes are the hydroxy aromatic dyes, i.e., dyes in which the auxochrome is a hydroxy group. Thus, a particularly preferred subclass of dyes are hydroxyaromatic azo dyes.

Representative dyes that can provide the dye moiety in the blocked dyes of this invention include the dyes of U.S. Pat. Nos. 3,230,085, 3,307,947, 3,579,334 and 3,684,513, referred to above, as well as the phenylazonaphthyl dyes of U.S. Pat. Nos. 3,929,760, 3,931,144, 3,932,380, 3,932,381, 3,942,987, 3,954,476, 4,001,204, and 4,013,635; the phenylazopyrazoline dyes of U.S. Pat. No. 4,013,633; the arylazopyrazolotriazole and arylazopyridinol dyes of Baigrie et al U.S. Pat. No. 4,142,891; the arylazo dyes of Landholm et al U.S. Pat. No. 4,156,609; the heterocyclylazonaphthol dyes of Chapman U.S. Pat. No. 4,207,104; the pyrimidylazopyrazole dyes of Green U.S. Pat. No. 4,148,641; the pyridylazonaphthol dyes of Anderson et al U.S. Pat. No. 4,147,544; the arylazopyridinol dyes of Chapman et al U.S. Pat. No. 4,148,642 and the arylazovinylol dyes of Chapman et al U.S. Pat. No. 4,148,643.

A preferred class of dyes of this invention can be represented by the structural formula

V

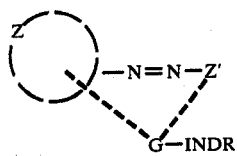

wherein:

Z represents the atoms necessary to complete an aromatic carbocyclic or heterocyclic nucleus containing at least one ring of 5 to 7 atoms (such as phenyl, naphthyl, pyridyl, pyrimidyl, indolyl, pyrazolyl, pyrazolotriazolyl, isoquinolyl and the like);

Z' represents a nucleus as defined for Z or an acyclic unsaturated group in conjugation with the azo group (such as vinyl, butadienyl, and the like);

G is the residue of an auxochromic group of the dye such as oxygen, sulfur, amino and the like); and INDR is as defined above.

It will be appreciated: (1) that G will be attached to Z or Z' in such a position that it is in resonance with the azo group; (2) that Z and Z' can be substituted with various groups known in the dye art; and (3) that by appropriate substitution of Z or Z' the dyes can be bisazo and trisazo dyes.

A preferred class of dyes of this invention are those designed for use in image transfer elements and processes. Such dyes contain a monitoring group which, in the presence of an alkaline processing solution and as a function of silver halide development, is responsible for a change in mobility of the dye. Such dyes are referred to herein as dye-providing compounds. Dye-providing compounds can be initially mobile, and rendered immobile as a function of silver halide development, as described, for example in U.S. Pat. Nos. 3,230,085, 3,307,947 and 3,579,334, referred to above. Alternatively, dye-providing compounds can be initially immobile and rendered mobile, in the presence of an alkaline processing solution, as a function of silver halide development. This latter class of dye-providing compounds are referred to as dye-releasing compounds. In such compounds the monitoring group is a carrier from which the dye is released as a function of silver halide development.

Preferred dye-releasing compounds of this invention can have structures analogous to structures I, III and V above as follows:

$$CAR-DYE'-G-INDR, \qquad VI$$

$$CAR-DYE'-G-E-X-NuP \text{ and} \qquad VII$$
$$\qquad VIII$$

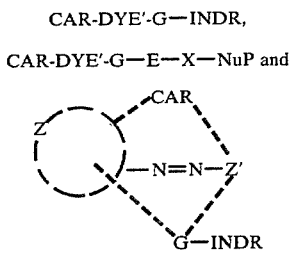

wherein:

CAR is a ballasted carrier moiety, linked to the dye and capable of being detached therefrom and thereby rendering the dye mobile under alkaline conditions as a function, direct or inverse, of development of a silver halide emulsion;

DYE'-G is the residue of a photographic image dye and

G, INDR, E, X, NuP, Z and Z' are as defined above.

There is great latitude in selecting a ballasted carrier moiety for incorporation in the dye releasing compounds of this invention. Depending upon the nature of the specific ballasted carrier moiety used, it may be attached, or linked, to the dye moiety through various groups. When the carrier moiety is cleaved from the dye moiety, cleavage may take place at such a location that a part of the carrier moiety remains attached to the dye moiety.

Ballasted carrier moieties useful in this invention include a variety of groups from which dye can be released by a variety of mechanisms. Representative ballasted carrier moieties are described, for example, in U.S. Pat. No. 3,227,550 and Canadian Patent No. 602,607 (release by chromogenic coupling); U.S. Pat. Nos. 3,443,939 and 3,443,940 (release by intramolecular ring closure); U.S. Pat. Nos. 3,628,952, 3,698,987, 3,725,062, 3,728,113, 3,844,785, 4,053,312, 4,055,428 and 4,076,529 (release after oxidation of carrier); U.S. Pat. No. 3,980,479, U.K. Pat. Nos. 1,464,104 and 1,464,105 and U.S. Pat. No. 4,199,355 (release unless carrier is oxidized); and U.S. Pat. No. 4,139,379 (release after reduction of carrier).

The ballasted carrier moiety can be such that a diffusible dye is released therefrom as a direct function of development of a silver halide emulsion. This is ordinarily referred to as negative-working dye release chemistry. Alternatively, the ballasted carrier moiety can be such that a diffusible dye is released therefrom as an inverse function of development of a silver halide emulsion. This is ordinarily referred to as positive-working dye release chemistry.

A preferred class of ballasted carrier moieties for use in negative-working dye release compounds of this invention are the ortho- or para-sulfonamidophenol and naphthol carriers described in U.S. Pat. Nos. 4,053,312, 4,055,428 and 4,076,529. In these compounds the dye moiety is attached through a sulfonamido group which is ortho or para to the phenolic hydroxy group and is released by hydrolysis after oxidation of the carrier moiety.

A preferred class of ballasted carrier moieties for use in positive-working dye release compounds, are the nitrobenzene and quinone carriers described in U.S. Pat. No. 4,139,379. In these compounds the dye moiety is attached to the carrier moiety via an electrophilic cleavage group ortho to the nitro group or the quinone oxygen such as a carbamate group and is released upon reduction of the carrier moiety.

A further preferred class of ballasted carrier moieties for use in positive-working dye release compounds are the hydroquinone carriers described in U.S. Pat. No. 3,980,479. In these compounds the dye moiety can be joined to a carbamate group ortho to one of the hydroquinone hydroxy groups.

A yet further preferred class of carriers for use in positive-working dye release compounds are the benzisoxazolone compounds described in U.K. Pat. Nos. 1,464,104 and 1,464,105. In these compounds the dye is attached to the carrier through an electrophilic group and is released unless a nucleophilic group adjacent the electrophilic group is oxidized.

The photographic reagents blocked in accordance with this invention can be any of the photographic reagents usefully incorporated in photographic compositions and elements which have a sulfur, oxygen, selenium, nitrogen or phosphorous atom available for derivatization with the blocking group. Such reagents include: development inhibitors such as benzotriazoles (the blocking group being joined to one of the ring nitrogen atoms) and thiotetrazoles, e.g. phenylmercaptotetrazole and ethylmercaptotetrazole (the blocking group being joined to the sulfur atom or a ring nitrogen atom); developing agents or electron transfer agents such as hydroquinones, aminophenols, p-phenylenediamines and pyrazolidones (the blocking group being joined to an oxygen or nitrogen atom); dye-forming couplers, DIR couplers and competing couplers such as pyrazolones, phenols and napthols (the blocking group being joined to an oxygen atom which activates the coupling position); DIR compounds such as cyclic ketones having the development inhibitor moiety alpha to the keto group (the blocking group being joined to the keto oxygen atom); silver halide solvents, silver halide complexing agents or silver halide fixing agents such as triazenethiones and thiazolinethiones (the blocking group being joined to the sulfur or nitrogen atom); and fogging agents or nucleating agents such as hydrazines and hydrazides (the blocking group being joined to the oxygen or nitrogen atom).

The following are examples of preferred compounds for use in the present invention.

A. Dye Releasing Compounds

1. Negative-Working Compounds

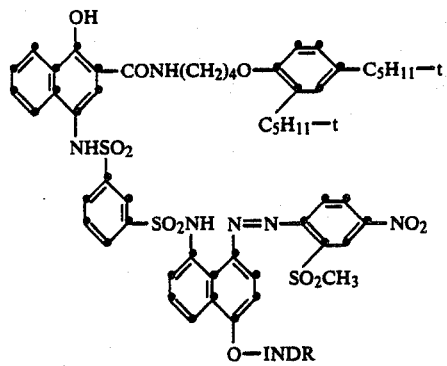

| Compound No. | INDR | Compound No. | INDR |
|---|---|---|---|
| 1 | -C(=O)-N(CH₃)-[phenyl-CH₂-O-C(=O)-CH₂Cl] | 2 | -C(=O)-N(phenyl)-CH₂CH₂-O-C(=O)-CCl₃ |
| 3 | -C(=O)-N(CH₃)-[phthalide] | 4 | -C(=O)-N(C₂H₅)-[phthalide] |
| 5 | -C(=O)-N(CH₃)-[phenyl-CH₂-N(CH₃)-C(=O)-CF₃] | 6 | -C(=O)-N(CH(CH₃)₂)-[succinimido-N-phenyl-SO₂NH₂] |

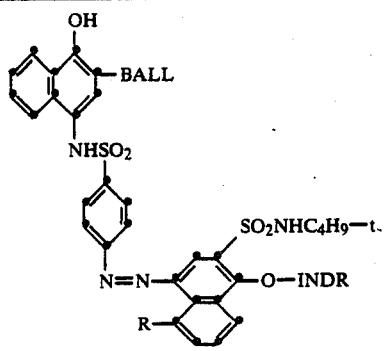

| Compound No. | INDR | BALL | R |

-continued

| | | | |
|---|---|---|---|
| 7 | (structure: -C(=O)-N(C2H5)- attached to isobenzofuranone) | -CONH(CH2)4O-C6H3(C5H11-t)2 | CH3SO2NH- |
| 8 | (structure: -C(=O)-N(C2H5)- attached to isobenzofuran) | -CON(C12H25-n)2 | CH3SO2NH- |

(Structure showing naphthalene with OH, CON(C18H37)2, NHSO2-, naphthalene with N=N-pyridine and O-INDR)

| Compound No. | INDR |
|---|---|
| 9 | (structure: -C(=O)-N(CH3)- attached to N-methylphthalimide) |

2. Positive-Working Compounds (Structure showing n-C12H25SO2, NO2, SO2C12H25-n substituted benzene with -C(=O)-N(CH3)-CH2- linked to phenyl with carbamate -O-C(=O)-N(CH3)- to SO2NH2-substituted benzene with N=N-azo to naphthalene bearing O-INDR and CH3)

| Compound No. | INDR |
|---|---|
| 10 | (structure: -C(=O)-N(CH3)-phenyl-CH2-N(CH3)-C(=O)-CF3) |

(Structure: quinone with R and R' substituents, bearing -C(=O)-N(CH3)-CH2- groups)

| Compound No. | R | R' | INDR |
|---|---|---|---|
| 11 | -C12H25-n | (structure with pyridine N=N-azo to methoxy/nitro benzene, NH2, O-INDR) | (structure: -C(=O)-N(CH3)-phenyl-CH2-N(CH3)-C(=O)-CF3) |

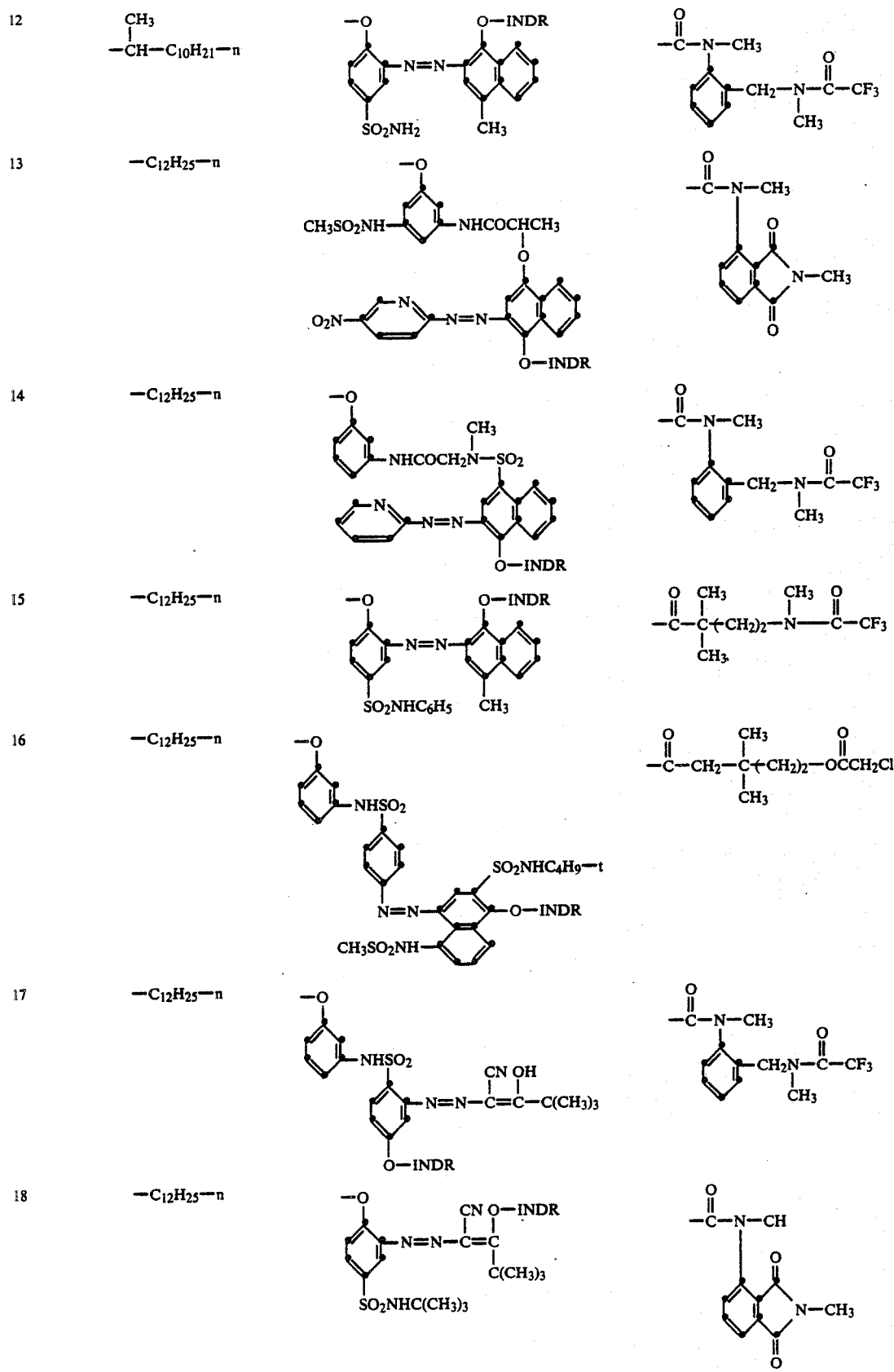
B. Other Dyes And Dye Providing Compounds.
Compound No. | Compound

-continued
| 19 | 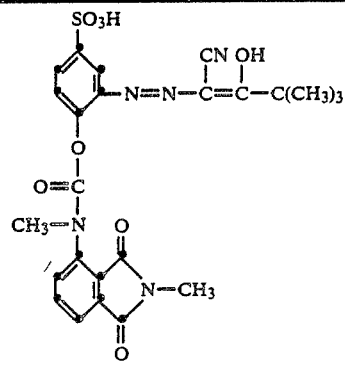 |
| 20 | 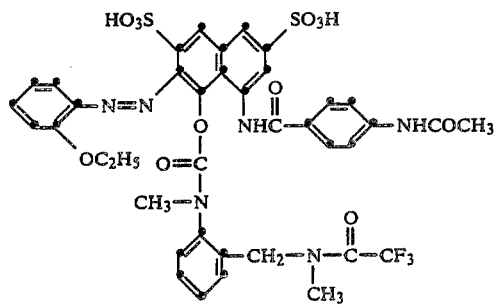 |
| 21 | 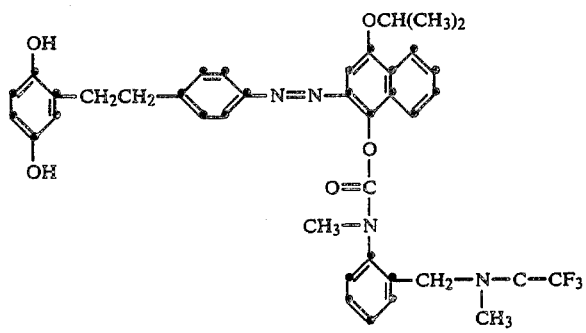 |
C. Development Inhibitors
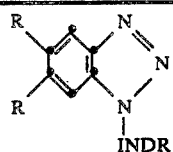
| Compound No. | R | INDR | Compound No. | R | INDR |
|---|---|---|---|---|---|
| 22 | Cl | =C(=O)—N(CH₃)—C₆H₄—CH₂—N(CH₃)—C(=O)—CF₃ | 23 | Cl | =C(=O)—N(CH₃)— (N-methylphthalimide) |
| 24 | H | =C(=O)—N(CH₃)— (N-methylphthalimide) | | | |

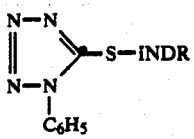

| Compound No. | INDR | Compound No. | INDR |
|---|---|---|---|
| 25 | -C(=O)-N(CH₃)- [phenyl with CH₂N(CH₃)C(=O)CF₃] | 26 | -C(=O)-N(CH₃)- [N-methylphthalimide] |
| 27 | -C(=O)-N-CH(CH₃)₂ [phthalide] | 28 | -C(=O)-N-CH(CH₃)₂ [phthalimide with p-C₆H₄SO₂NH₂] |
| 29 | -CON(CH₃)- [phenyl substituted with NHSO₂-p-C₆H₄CH₃ and CH₂N(CH₃)COCF₃] | 30 | -CON(i-C₃H₇)- [phenyl-O-CH₂-N(phthalimide)] |

D. Developing Agents and Electron Transfer Agents

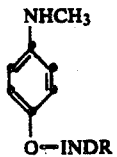

| Compound No. | INDR | Compound No. | INDR |
|---|---|---|---|
| 31 | -C(=O)-N(CH₃)- [phenyl with CH₂N(CH₃)C(=O)CF₃] | 32 | -C(=O)-N(CH₃)- [N-methylphthalimide] |

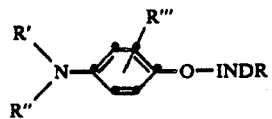

| Compound No. | R' | R" | R''' | INDR |
|---|---|---|---|---|
| 33 | —(CH₂)₄— | | H | -CO-N(i-C₃H₇)- [CH with phthalimide and C₆H₄SO₂NH-C₃H₇-i] |
| 34 | —(CH₂)₄— | | H | -CO-N(CH₃)- [phenyl with NHSO₂CH₃ and CH₂N(CH₃)COCF₃] |

-continued

| | | | | |
|---|---|---|---|---|
| 35 | H | CH$_3$SO$_2$NH—p-C$_6$H$_4$—CH$_2$— | 3-n-C$_{15}$H$_{31}$ | —CON(i-C$_3$H$_7$)—CO—CH$_2$—CO—N—C$_6$H$_4$—SO$_2$NH—C$_3$H$_7$-i |
| 36 | H | n-C$_{10}$H$_{21}$SO$_2$NH—p-C$_6$H$_4$CH$_2$— | 2-OCH$_3$ | " |
| 37 | H | H | 2,6-(OCH$_3$)$_2$ | —CON(i-C$_3$H$_7$)—CO—CH$_2$—CO—N—C$_2$H$_5$ |

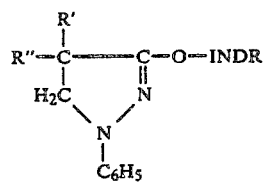

| Compound No. | R' | R" | INDR |
|---|---|---|---|
| 38 | —H | —H | (C(=O)N(CH$_3$)-C$_6$H$_4$-CH$_2$-N(CH$_3$)-C(=O)CF$_3$) |
| 39 | —CH$_3$ | —CH$_3$ | (C(=O)N(CH$_3$)-C$_6$H$_4$-CH$_2$-N(CH$_3$)-C(=O)CF$_3$) |
| 40 | —CH$_3$ | —CH$_2$—OH | (C(=O)N(CH$_3$)-C$_6$H$_4$-CH$_2$-N(CH$_3$)-C(=O)CF$_3$) |
| 41 | —CH$_3$ | —CH$_2$—OH | (C(=O)N(CH$_3$)-phthalimide-N—CH$_3$) |
| 42 | —CH$_3$ | —CH$_3$ | (C(=O)N(CH$_3$)-phthalimide-N—CH$_3$) |
| 43 | —H | —H | (C(=O)N(CH$_3$)-phthalimide-N—CH$_3$) |

-continued

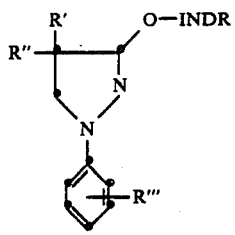

| Compound No. | R' | R'' | R''' | INDR | R | B |
|---|---|---|---|---|---|---|
| 44 | H | H | H | —CON(CH$_3$)—C$_6$H$_3$(B)(CH$_2$N(CH$_3$)COCF$_3$) | | NHSO$_2$—p-C$_6$H$_4$CH$_3$ |
| 45 | H | H | p-CH$_3$ | ↓ | | ↓ |
| 46 | H | H | p-C$_2$H$_5$ | ↓ | | ↓ |
| 47 | H | H | p-C$_3$H$_7$—n | ↓ | | ↓ |
| 48 | CH$_3$ | CH$_3$ | H | ↓ | | ↓ |
| 49 | CH$_3$ | CH$_2$OH | H | ↓ | | ↓ |
| 50 | H | i-C$_3$H$_7$ | H | ↓ | | ↓ |
| 51 | H | i-C$_3$H$_7$ | p-CH$_3$ | ↓ | | NHSO$_2$CH$_3$ |
| 52 | H | H | H | ↓ | | ↓ |
| 53 | CH$_3$ | CH$_2$OH | H | ↓ | | ↓ |
| 54 | H | H | p-CH$_3$ | ↓ | | SO$_2$NHCH$_3$ |
| 55 | CH$_3$ | CH$_2$OH | p-CH$_3$ | ↓ | | SO$_2$NHCH$_3$ |
| 56 | H | H | H | ↓ | | SO$_2$NHC$_6$H$_5$ |
| 57 | H | H | p-CH$_3$ | ↓ | | SO$_2$NH$_2$ |
| 58 | H | H | H | ↓ | | H |
| 59 | H | H | H | ↓ | H | H |
| 60 | H | H | H | —CON(CH$_3$)—C$_6$H$_3$(B)(CH$_2$OR) | | |
| 61 | H | H | H | ↓ | H | NHSO$_2$CH$_3$ |
| 62 | H | H | p-CH$_3$ | ↓ | H | H |
| 63 | H | H | H | ↓ | COCH$_2$Cl | H |
| 64 | H | H | H | ↓ | CHO | H |
| 65 | H | H | p-CH$_3$ | ↓ | CHO | H |
| 66 | H | H | p-C$_3$H$_7$—n | —CON(CH$_3$)— (coumarin with SO$_2$NHC$_4$H$_9$—t) | | |

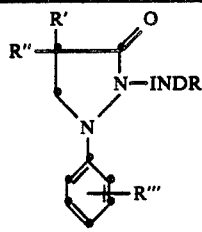

| Compound No. | R' | R'' | R''' | INDR | R | B |
|---|---|---|---|---|---|---|
| 67 | H | H | H | —CON(CH$_3$)—C$_6$H$_3$(B)(CH$_2$N(CH$_3$)COCF$_3$) | | NHSO$_2$—p-C$_6$H$_4$—CH$_3$ |
| 68 | H | H | p-CH$_3$ | " | | NHSO$_2$CH$_3$ |
| 69 | H | H | H | —CON(CH$_3$)—C$_6$H$_3$(CH$_2$OR) | CHO | |
| 70 | H | H | p-CH$_3$ | ↓ | CHO | |
| 71 | H | H | H | ↓ | COCH$_2$Cl | |
| 72 | H | H | p-CH$_3$ | ↓ | COCH$_2$Cl | |

-continued
| | | | | |
|---|---|---|---|---|
| 73 | H | H | H | 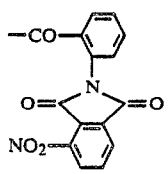 |
| Compound No. | INDR | Compound No. | INDR |
|---|---|---|---|
| 74 | 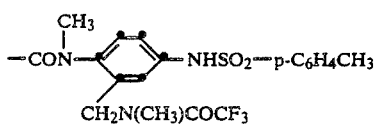 | 75 | 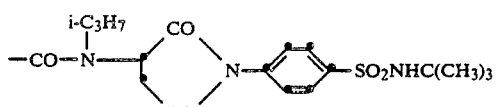 |
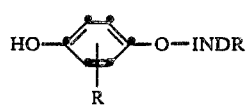
| Compound No. | R | INDR |
|---|---|---|
| 76 | H | 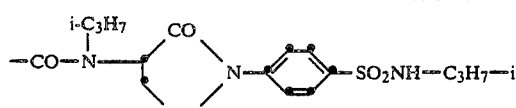 |
| 77 | t-C$_4$H$_9$ | 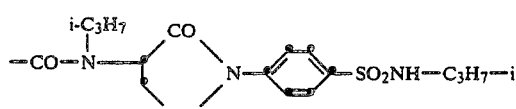 |
| 78 | p-C$_6$H$_4$CH$_3$ | 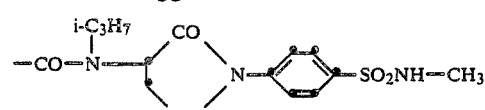 |
| 79 | t-C$_4$H$_9$ | 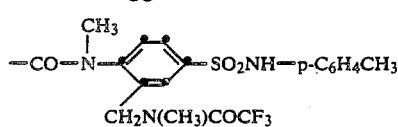 |
| 80 | t-C$_4$H$_9$ | 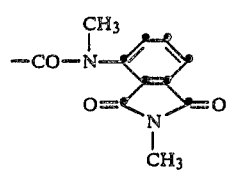 |
| 81 | p-C$_6$H$_4$CH$_3$ | 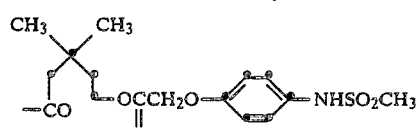 |
| 82 | p-C$_6$H$_4$CH$_3$ | 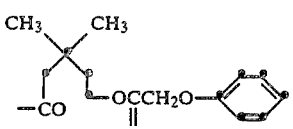 |
| 83 | p-C$_6$H$_4$CH$_3$ | 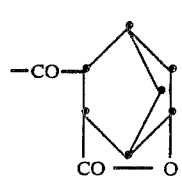 |

-continued
| | | |
|---|---|---|
| 84 | p-C$_6$H$_4$CH$_3$ | 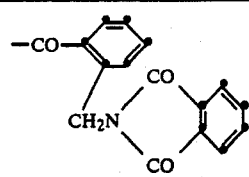 |
| 85 | p-C$_6$H$_4$CH$_3$ | 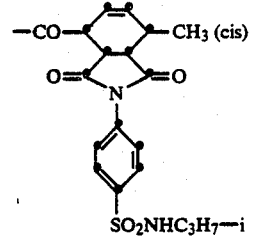 |
| 86 | t-C$_4$H$_9$ | 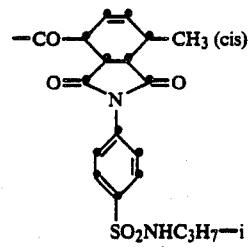 |
| 87 | p-C$_6$H$_4$CH$_3$ | 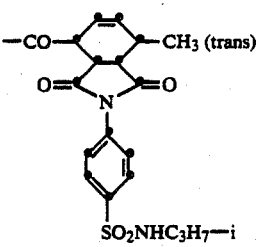 |
| 88 | 2,6-(OCH$_2$C$_6$H$_5$)$_2$ | 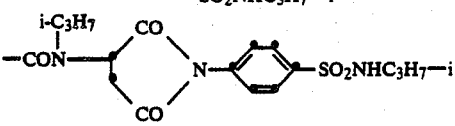 |
E. Couplers
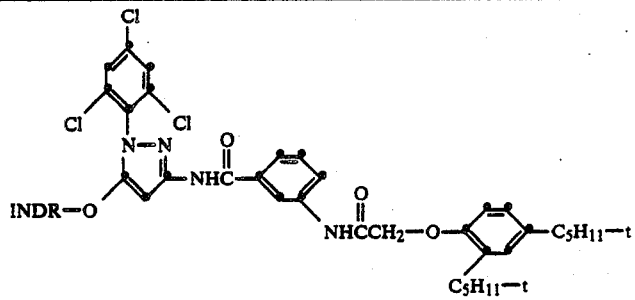
| Compound No. | INDR | Compound No. | INDR |
|---|---|---|---|
| 89 | 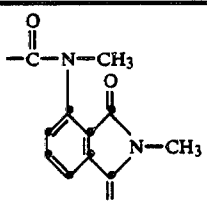 | 90 | 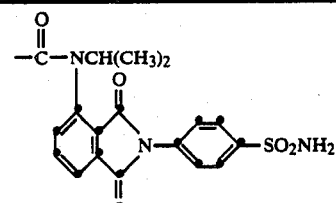 |
| 91 | 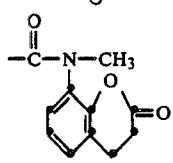 | 92 | 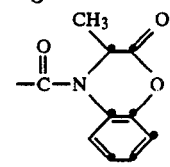 |

F. Bleach Inhibitors

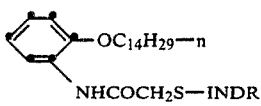

| Compound No. | INDR |
|---|---|
| 93 | 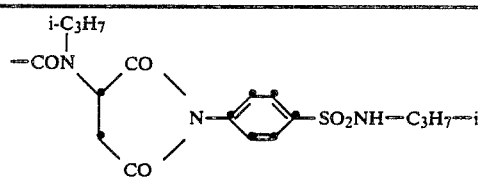 |

G. Nucleating Agents

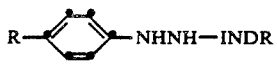

| Compound No. | R | INDR | Compound No. | R | INDR |
|---|---|---|---|---|---|
| 94 | —NHCOC$_5$H$_{11}$—n | 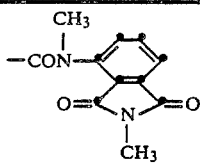 | 95 | —NHCOC$_5$H$_{11}$—n | 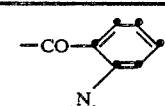 |
| 96 | —CH$_3$ | 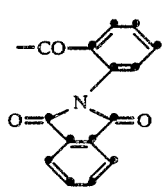 | 97 | —(CH$_2$)$_2$NHSO$_2$CH$_3$ | 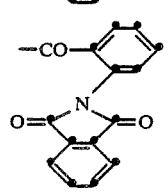 |

The compounds of this invention can be prepared in modular, stepwise fashion using chemical reactions known to those skilled in the art. Generally the preformed dye or photographic reagent is condensed with a precursor of the blocking group. When the dye contains a carrier, the carrier may be attached to the dye before or after reaction with the blocking group. The examples which follow show suitable techniques for preparing compounds of this invention.

The photographic elements in which the photographic image dyes and photographic reagents of this invention are incorporated can be simple elements comprising a support bearing a layer of the photographic dye or reagent. Preferred elements contain a silver halide emulsion layer and especially preferred are multilayer multicolor silver halide elements.

The blocked photographic reagents of this invention can be employed with photographic elements and film units in the ways and for the purposes which photographic reagents have previously been employed with photographic elements and film units. For example, if the reagent is a development inhibitor, it can be used to suppress development of silver halide, especially in minimum density areas of the image. If the photographic reagent is a bleach inhibitor, it can be used to inhibit bleaching of silver during a subsequent processing step. If the photographic reagent is a silver halide solvent or complexing agent, it can be used to enchance removal of silver halide from the element or film unit during a subsequent processing step or to assist migration of silver halide in the element or film unit. If the photographic reagent is a developing agent or electron transfer agent, it can be used to effect or assist development of silver halide. If the photographic reagent is a nucleating agent, it can be used to alter the developability of silver halide. Still other ways in which the released photographic reagent can be employed in photographic elements, film units and processes will be apparent to those skilled in the art.

The blocked photographic reagents can be incorporated in photographic elements and film units by techniques available in the art. In certain preferred embodiments the blocked photographic reagent is first dissolved in a high-boiling solvent, such as a water-insoluble coupler solvent, and then dispersed in a carrier material. Typical useful coupler solvents are moderately polar solvents such as tri-o-tolyl phosphate, di-n-butyl phthalate, diethyllauramide, 2,4-diamylphenol, liquid dye stabilizers such as described in an article entitled "Improved Photographic Dye Image Stabilizer-Solvent", *Product Licensing Index*, Vol. 83, March, 1971, and the like. (*Product Licensing Index* is published by Industrial Opportunities Ltd., Homewell, Havant Hampshire, PO9 1EF, United Kingdom.)

Depending upon the particular photographic reagent, and the purpose for which it is being used, it may be a part of a photographic film unit but on a support separate from the photosensitive element (e.g., in a separate cover sheet, process sheet or receiver element) and be brought into contact with the photosensitive layer of the photosensitive element or film unit but in a location other than a photosensitive layer e.g., in an adjacent layer or in a layer of mask adhesive.

A photographic image dye blocked in accordance with this invention is preferably incorporated in the silver halide emulsion layer in order to obtain the benefits associated with shifting the spectral absorption of the dye. However, if desired, the image dye can be incorporated in another layer of the element, or it can be in a layer on a separate support which is brought into contact with the silver halide emulsion layer prior to or during development.

A typical multilayer multicolor photographic element containing blocked image dyes according to this invention can comprise a support having thereon a red-sensitive silver halide emulsion unit having associated therewith a cyan-dye-image-providing material, a green-sensitive silver halide emulsion unit having associated therewith a magenta-dye-image-providing material and a blue-sensitive silver halide emulsion unit having associated therewith a yellow-dye-image-providing material, at least one of the silver halide emulsion units having associated therewith a photographic image dye of the invention. Each silver halide emulsion unit can be composed of one or more layers and the various units and layers can be arranged in different relationships with respect to one another in accordance with configurations known in the art.

A typical multilayer multicolor photographic element containing a blocked photographic reagent in accordance with this invention can comprise a support having thereon a red-sensitive silver halide emulsion unit having associated therewith a cyan-dye-image providing material, a green-sensitive silver halide emulsion unit having associated therewith a magenta-dye-image-providing material and a blue-sensitive silver halide emulsion unit having associated therewith a yellow-dye-image-providing material, the element containing a blocked photographic reagent of this invention. Each silver halide emulsion unit can be composed of one or more layers and the various units and layers can be arranged in different relationships with respect to one another in accordance with configurations known in the art. The various dye-image-providing materials are those commonly employed in color photographic elements, and include dye-forming couplers, dye developers and dye releasers, including materials blocked in accordance with this invention.

The elements of the invention can contain additional layers conventional in photographic elements, such as spacer layers, filter layers, antihalation layers, scavenger layers and the like and an appropriate blocked photographic reagent can be contained in such layers. The support can be any suitable support used with photographic elements. Typical supports include polymeric films, paper (including polymer-coated paper), glass and the like.

The light-sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide, and mixtures thereof. The emulsions can be negative working or direct positive emulsions. They can form latent images predominantly on the surface of the silver halide grains or predominantly in the interior of the silver halide grains. They can be chemically and spectrally sensitized in accordance with usual practices. The emulsions typically will be gelatin emulsions although other hydrophilic colloids can be used in accordance with usual practice.

The photographic dyes of this invention can be incorporated in the silver halide emulsions, or in other vehicles used in the photographic elements, in the same way as photographic image dyes have been incorporated in such emulsions and vehicles in the past. Depending upon the physical properties of the photographic image dye and its physical compatibility with the emulsion or vehicle, it can be dispersed directly therein, it can be mixed with organic or aqueous solvents and then dispersed in the emulsion or vehicle, or it can be loaded in a latex which is then dispersed in the emulsion or vehicle. The latter technique is described in *Research Disclosure*, July 1977, Item 15930. *Research Disclosure* is published by Industrial Opportunities Limited, Homwell, Havant, Hampshire, PO9 1EF UK.

Further details regarding silver halide emulsions and elements and addenda incorporated therein can be found in *Research Disclosure*, December 1971, Item 9232.

Photographic images can be prepared with photographic elements of this invention by a variety of techniques. Those elements which contain a blocked photographic reagent will depend for image formation primarily on the image producing component of the element. This can be silver halide, a color forming coupler or a dye-releasing compound.

Thus, photographic images can be prepared with the photographic elements of this invention by processing the element in accordance with known procedures for processing photographic elements containing preformed image dyes. Silver dye bleach processing can be employed as described, for example, in U.S. Pat. No. 3,684,513, Mees and James, *The Theory of the Photographic Process*, pages 384 and 395, Third Edition, 1966, The MacMillan Co., or Friedman, *History of Color Photography*, pages 405–429, 1944. Photographic elements designed for providing photographic images by diffusion transfer processes can be processed as described in the numerous patents and articles relating thereto, a number of which have been referred to herein in connection with the discussion of photographic image dyes.

Inasmuch as the processes used with silver halide emulsions employ alkaline processing solutions for development or for other purposes, the blocked image dyes of this invention will be shifted to the desired color and the blocked photographic reagent released concurrent with other processing steps.

As indicated above, a particularly preferred class of dyes of this invention are dye-releasing compounds which are nondiffusible as coated in the photographic element but which upon processing release a diffusible dye. The following is a description of preferred photographic processes, photographic elements and photographic film units particularly adapted for the use of dye-releasing compounds. In this discussion the compounds are referred to alternatively as dye-releasing compounds, nondiffusible dye-releasing compounds, or nondiffusible compounds.

Photographic color images can be formed with the nondiffusible dye-releasing compounds of this invention by treating an imagewise exposed element containing the dye-releasing compound with an alkaline processing solution to form an imagewise distribution of diffusible dye as a function of the imagewise exposure of the silver halide emulsion. Images can be formed employing the imagewise released diffusible dye, or the remaining imagewise distribution of nondiffusible compound, or both.

The released diffusible dye can be allowed to diffuse to a receiver sheet or layer to form a transfer image. Alternatively, it can be removed from the element and not used further.

Whether the imagewise distribution of diffusible dye is used to form an image or not, the remaining non-diffusible compound can be used as a retained image in the layer in which it was initially coated. This could include removing residual silver and silver halide by any conventional procedure known to those skilled in the art, such as a bleach bath followed by a fix bath, a bleach-fix bath, etc. It will be noted that alkaline processing of the element unblocks the dye and shifts its spectral absorption, so that the retained image has the desired color.

Alternatively, once the initially formed diffusible dye is removed from the element, the residual non-diffusible compound can be employed to form a transfer image by treating it to yield a second distribution of diffusible dye which can be transferred to a suitable receiver sheet or layer.

Accordingly, a preferred process for producing a photographic image in color according to this invention comprises:

(a) treating an imagewise-exposed photographic element, as described above, with an alkaline processing composition in the presence of a silver halide developing agent to effect development of each of the exposed silver halide emulsion layers, thereby (b) releasing imagewise a diffusible dye as a function of the development of each of the silver halide emulsion layers; and (c) diffusing at least a portion of the imagewise distribution of diffusible dye out of the layer in which it is coated.

The alkaline processing composition employed in this embodiment can be an aqueous solution of an alkaline material, such as an alkali metal hydroxide or carbonate (e.g. sodium hydroxide or sodium carbonate) or an amine (e.g. diethylamine). Preferably the alkaline composition has a pH in excess of 11. Suitable materials for use in such compositions are disclosed in *Research Disclosure*, pages 79–80, November 1976.

Preferably the developing agent is contained in the alkaline processing composition, although it can be contained in a separate solution or process sheet, or it can be incorporated in a layer of the photographic element or film unit. When the developing agent is separate from the alkaline processing composition, the alkaline composition serves to activate the developing agent and provide a medium in which the developing agent can contact and develop developable silver halide.

A variety of silver halide developing agents can be used with the elements of this invention. The choice of a particular developing agent will, to some extent, depend on the ballasted carrier moiety. Suitable developing agents can be selected from such compounds as hydroquinone, aminophenols, (e.g., N-methylaminophenol), 1-phenyl-3-pyrazolidone, 1-phenyl-4,4-dimethyl-3-pyrazolidone, 1-phenyl-4-methyl-4-hydroxymethyl-3-pyrazolidone, N,N-diethyl-p-phenylenediamine, 3-methyl-N,N-diethyl-p-phenylenediamine, 3-methoxy-N,N-diethyl-p-phenylenediamine, N,N,N',N'-tetramethyl-p-phenylenediamine, etc. The non-chromogenic developers in this list are preferred, since they have a reduced propensity to stain dye image-receiving layers.

A photographic film unit which can be processed in accordance with this invention, and which is adapted to be processed by passing the unit between a pair of juxtaposed pressure-applying members, such as would be found in a camera designed for in-camera processing, comprises:

(a) a photographic element, as described above;

(b) a dye image-receiving layer; and (c) an alkaline processing composition contained within means from which it can be discharged within the film unit;

the film unit containing a silver halide developing agent and a dye releasing compound or photographic reagent blocked in accordance with this invention.

As indicated previously, the developing agent is preferably incorporated in the alkaline processing composition, although it can be contained in a layer of the film unit. If contained in such a layer, it can be blocked in accordance with this invention.

Preferably, the alkaline processing composition is introduced into reactive association with other components of the film unit from a rupturable container which is adapted to be positioned during processing of the film unit so that a compressive force applied to the container by pressure-applying members will rupture the container and effect a discharge of the containers contents within the film unit. However, other methods of introducing the alkaline processing composition can be employed, e.g., injecting processing solution with communicating members similar to hypodermic syringes which are attached either to a camera or camera cartridge.

Preferred rupturable containers are described in U.S. Pat. Nos. 2,543,181; 2,643,886; 2,653,732; 2,723,051; 3,056,492; 3,056,491 and 3,152,515. In general, such containers comprise a rectangular sheet of fluid- and air-impervious material folded longitudinally upon itself to form two walls which are sealed to one another along their longitudinal and end margins to form a cavity in which processing solution is contained.

Any material can be employed as the image-receiving layer in the film units of this invention as long as it will mordant, or otherwise fix, the dyes which diffuse to it. The particular material chosen will, of course, depend upon the dyes to be mordanted. Suitable materials are disclosed in *Research Disclosure*, November 1976 pages 80–82. The image-receiving layer can contain ultraviolet absorbers to protect the dye images from fading due to ultraviolet light, brighteners and similar materials used to protect or enhance photographic dye images.

Additional layers can be incorporated in film units of this invention. These include pH lowering layers (sometimes referred to as acid layers or neutralizing layers), timing or spacing layers, opaque light-reflecting layers, opaque light-absorbing layers, scavenger layers, and the like. Suitable blocked photographic reagents can be incorporated in such layers.

A layer of a pH-lowering material in the film unit will usually increase the stability of the transferred image. Generally, the pH-lowering material will effect a reduction in the pH of the image layer from about 13 or 14 to at least 11 and preferably to 5 to 8 within a short time after introduction of the alkaline processing composition. Suitable materials and their functioning are disclosed in *Research Disclosure*, July 1974, pages 22 and 23 and *Research Disclosure*, July 1975, pages 35–37.

A timing or inert spacer layer can be employed in the film units of this invention. Such a layer can be associated with the pH-lowering layer to control pH reduction as a function of the rate at which alkali diffuses through the timing layer. Examples of such timing layers and their functioning are disclosed in the Research Disclosure articles mentioned in the immediately preceding paragraph.

Alkaline-solution-permeable, substantially opaque, light-reflective layers, which can be employed in certain embodiments of film units of this invention are described in *Research Disclosure*, November 1976, page 82.

Various formats for diffusion transfer film units are known in the art. The layer arrangement employed with them can be used in the film units of this invention. In one useful format the dye image-receiving layer of the film unit is located on a separate support adapted to be superposed on the photographic element after exposure thereof. Such image-receiving layers are generally disclosed, for example, in U.S. Pat. No. 3,362,819.

In another useful format the dye image-receiving layer is located integral with the photographic element and is positioned between the support and the lowermost silver halide emulsion layer. One such format is disclosed in Belgian Patent No. 757,960. In such a format, the support for the photographic element is transparent and bears, in order, an image-receiving layer, a substantially opaque light-reflective layer, and then the photosensitive layer or layers. After imagewise exposure, a rupturable container containing the alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer and dye images, formed as a function of development, diffuse to the image-receiving layer to provide a right-reading image which is viewed through the transparent support on the opaque reflecting layer backgrounds. For other details concerning the format of this particular integral film unit, reference is made to the above-mentioned Belgian Patent No. 757,960.

Another format is disclosed in Belgian Patent No. 757,959. In this embodiment, the support for the photographic element is transparent and bears, in order, the image-receiving layer, a substantially opaque, light-reflective layer and the photosensitive layer or layers. A rupturable container, containing an alkaline processing composition and an opacifier, is positioned between the uppermost emulsion layer and a transparent top sheet which has thereon a neutralizing layer and a timing layer. The film unit is placed in a camera exposed through the transparent top sheet and then passed through a pair of pressure-applying members in the camera as it is being removed therefrom. The pressure-applying members rupture the container and spread processing composition and opacifier over the photographic layers to commence development and protect the photosensitive layers from further light exposure. The processing composition develops each silver halide layer and dye images, formed as a result of development, diffuse to the image-receiving layer to provide a right-reading image which is viewed through the transparent support on the opaque reflecting layer background. For further details concerning the format of this particular integral film unit, reference is made to the above-mentioned Belgian Patent No. 757,959.

Still other useful formats in which this invention can be employed are described in U.S. Pat. Nos. 3,415,644; 3,415,645; 3,415,646; 3,647,437; 3,635,707; and 3,993,486.

The term "nondiffusible" used herein has the meaning commonly applied to the term in photography and denotes materials that for all practical purposes do not migrate nor wander through organic colloid layers such as gelatin in an alkaline medium, in the photographic elements of the invention and preferably when processed in a medium having a pH of 11 or greater. The same meaning is to be attached to the term "immobile." The term "diffusible" as applied to the materials of this invention has the converse meaning and denotes materials having the property of diffusing effectively through the colloid layers of the photographic elements in an alkaline medium. "Mobile" has the same meaning.

The term "associated therewith" as used herein is intended to mean that the materials can be in either the same or different layers so long as the materials are accessible to one another during processing.

The following examples further illustrate this invention.

Example 1—Preparation of Compound 1

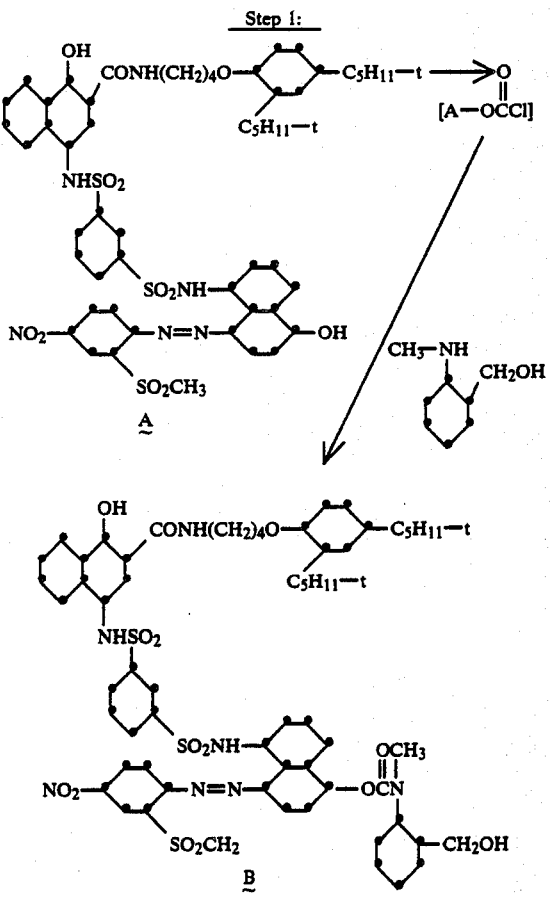

A mixture of A (5.4 g, 5 mmol) and dicyclohexylethylamine (1.05 g, 5 mmol) in 75 ml of dichloromethane and 10 ml of tetrahydrofuran was cooled to $-80°$ C. Phosgene (5 ml of $12\frac{1}{2}\%$ solution in benzene, 5 mmol) was added and allowed to react for about 30 minutes. o-Methylaminobenzyl alcohol (1.37 g, 10 mmol) was then added. After 5 minutes, 1 ml of pyridine was added and the mixture was allowed to warm to room temperature. The mixture was washed with dilute hydrochloric acid before the organic phase was concentrated to an oil. The oil was dissolved in 25 ml of dichloromethane plus 1 ml of acetic acid and filtered through diatomaceous earth. Elution with 1% acetic acid in dichloromethane from a column of silica gel, pretreated with 25 ml acetic acid in 80 ml of dichloromethane yielded 1.4 g of product B, Anal. Calcd. for $C_{63}H_{67}N_7O_{14}S_3$: C, 60.9; H, 5.4; N, 7.9; S, 7.7. Found: C, 61.0; H, 5.5; N, 8.2; S, 7.9.

Step 2:

B ⟶ Compound 1

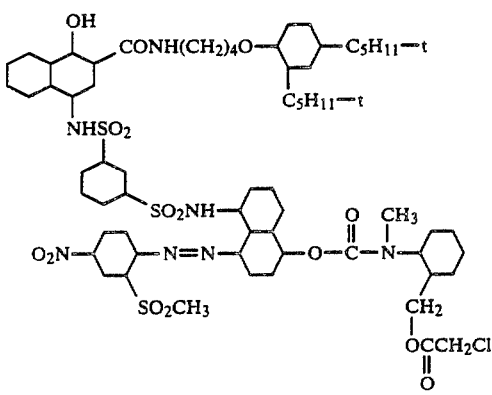

A solution of B (7.0 g, 5.6 mmol) in 50 ml of tetrahydrofuran was cooled to 0° C. Chloroacetyl chloride (2.5 ml) was added to the solution followed by pyridine (1.0 ml). After the mixture was stirred for 20 minutes, 20 ml of water was added to hydrolyze the excess acid chloride. The mixture was distributed between ether and water. Chloroacetic acid was removed by washing with 0.2 N sodium carbonate and then with water. Silica gel chromatography (dichloromethane/ethyl ether eluent) yielded 4 g of Compound 1 as a glass. Anal. Calcd. for $C_{65}H_{68}ClN_7O_{15}S_3$: C, 59.2; H, 5.2; Cl, 2.7; N, 7.4; S, 7.3. Found: C, 58.9; H, 5.3; Cl, 2.8; N, 7.3; S, 6.9.

Example 2—Preparation of Compound 9

Part 1: Preparation of the Blocking Group

Step 1:

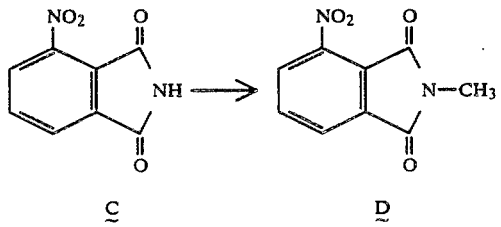

Compound C (19.2 g, 0.1 m), methyl iodide (10.3 ml, 2.28 m) and potassium carbonate (20.7 g, 0.15 m) are suspended in acetone and stirred and refluxed for 16 hours. After cooling, the salts are removed by filtration and the filtrate is concentrated under reduced pressure. The resulting solid is dissolved in ethyl acetate, washed with water, dried over magnesium sulfate and concentrated under reduced pressure to a solid. The product is recrystallized from ethanol to yield 12.4 g, m.p. 102°–104° C. of D.

Anal. Calcd. for $C_9H_6N_2O_4$: C, 52.4; H, 2.9; N, 13.6. Found: C, 52.3; H, 2.6; N, 14.1.

Step 2:

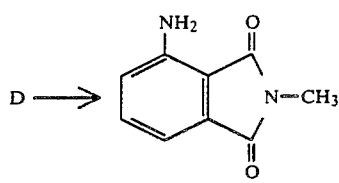

Compound D (2.06 g, 0.01 m) is dissolved in 150 ml of tetrahydrofuran, treated with one teaspoon of 10% palladium on carbon catalyst and shaken under a hydrogen atmosphere for one hour. There is an uptake of 2.5 p.s.i. of hydrogen. The catalyst is filtered off and the solvent is removed under reduced pressure to give 1.6 g of compound E.

Step 3:

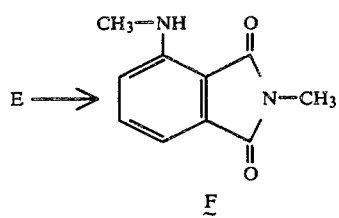

Compound E (4.4 g, 0.025 m) is dissolved in 40 ml of dry methanol, then formaldehyde (20.2 ml of a 37% solution, 0.025 m) and acetic acid (7.15 ml, 0.125 m) are added. The resulting mixture is stirred for three hours at room temperature. After cooling to 0° C., sodium cyanoborohydride (1.55 g, 0.025 m) is added slowly so that the temperature does not rise above 5° C. After stirring for 16 hours at room temperature, the mixture is poured into water and neutralized with sodium bicarbonate. The resulting solution is extracted with ethyl acetate, dried over sodium sulfate and the solvent removed under reduced pressure to give a dark green solid. This product is recrystallized from 30 ml of ethanol to yield 2.5 g of green needles, compound F, m.p. 147°–149° C. Anal. Calcd. for $C_{10}H_{10}N_2O_2$: C, 63.1; H, 5.3; N, 14.7; Found: C, 63.0; H, 5.4; N, 15.0.

Step 4:

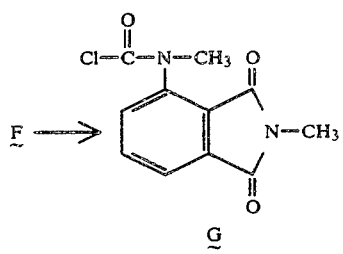

Compound F (1.90 g, 0.01 m) and diisopropylethyl amine (1.41 g, 0.011 m) are dissolved in 50 ml dry tetrahydrofuran and added dropwise over 15 minutes to a phosgene-in-benzene solution (10 ml, 0.01 m) at 0° C. At the end of the one hour, thin-layer chromatography shows incomplete reaction. Another portion (5 ml, 0.005 m) of the phosgene-in-benzene solution is added and the cooling bath is removed. The solution is stirred an additional two hours. The solvent is removed under reduced pressure, the residue is added to ice and hydrochloric acid, and the resulting solution is extracted with ethyl acetate. The extracts are dried over sodium sulfate and concentrated under reduced pressure to give a yellow oil that crystallized when kept under reduced pressure to give blocking group G, m.p. 93°-95° C.

Part 2 Attachment of the Blocking Group to the Dye

Step 1:

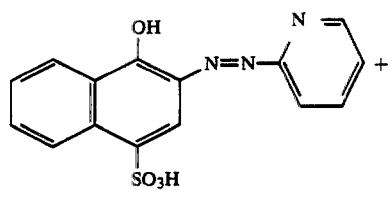

H

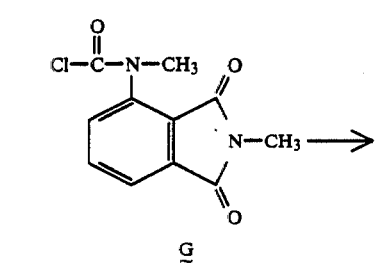

G

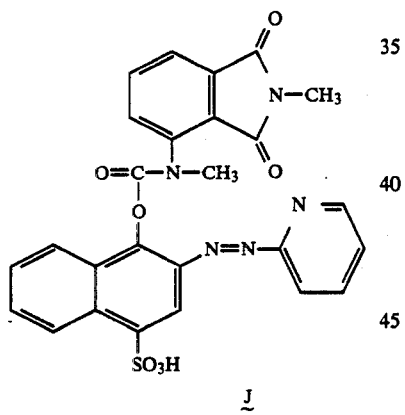

J

The preparation of H is described in U.S. Ser. No. 832,309, filed Apr. 3, 1978 on page 37.

Compound H (19.74 g, 0.06 m) is dissolved in 200 ml of dry pyridine and diisopropylethyl amine (24 ml, 0.15 m) is added. Compound G (25.3 g, 0.1 m) is then added and the reaction mixture is stirred at room temperature for 16 hours. The color of the reaction mixture changes from deep red to yellow during this time.

The reaction mixture is poured into 1 liter of hexane:ethyl ether (1:1) resulting in the formation of a red oil. The solvents are removed by decantation and the oil is triturated several times with ethyl ether. Two liters of water and just enough hydrochloric acid to turn litmus paper red are added. The orange solid that separates is collected and dried under vacuum at 60° C. overnight to yield 31.8 g of compound J.

Step 2:

-continued

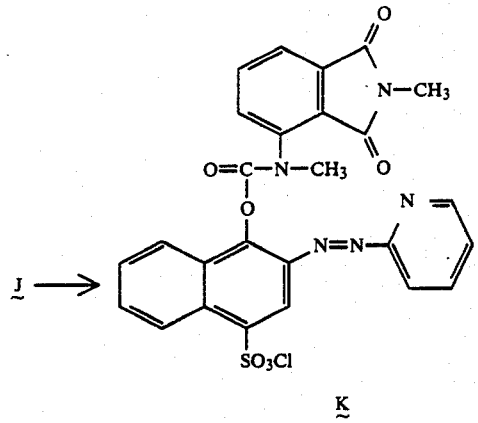

K

Compound J (31.8 g, 0.06 m) is stirred in a mixture of 200 ml of thionyl chloride and 2 ml of N,N-dimethylformamide. After complete solution is obtained, an orange precipitate separates and then slowly goes into solution as the reaction proceeds. The reaction mixture is stirred for six hours, then poured into hydrochloric acid and ice. The mixture is extracted with ethyl acetate, the extracts are dried over magnesium sulfate and the solvent is removed under reduced pressure to yield a red solid, compound K, that is triturated with hexane and used directly in the next step.

Part 3 Attachment of the Blocked Dye to the Carrier

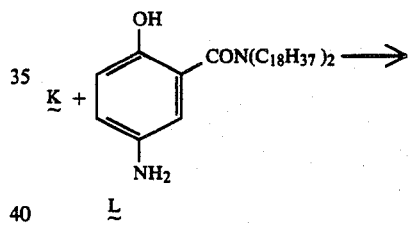

L

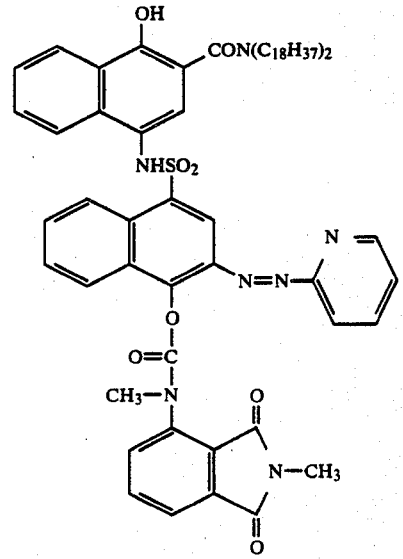

Compound 9

Compound L (35.4 g, 0.05 m) is dissolved in 350 ml of dry tetrahydrofuran and 70 ml of dry pyridine and cooled to 0° C. While stirring under nitrogen, compound K (28.2 g, 0.05 m) is added and the reaction mixture is stirred at ambient temperature 16 hours. The reaction mixture is poured into hydrochloric acid and ice, the precipitated solid is collected and air dried.

The solid is purified by chromatography on silica gel using hexane:ethyl ether (1:1) as eluent. The large orange band is collected and the solvent is removed under reduced pressure. A solid product, compound 9, is obtained from ligroin: yield 25 g.

Anal. Calcd. for $C_{73}H_{99}N_7O_8S$: C, 71.0; H, 8.1; N, 7.9; S, 2.6. Found C, 71.3; H, 8.3; N, 8.1; S, 2.6.

Example 3—Preparation of Compound 16

Part 1: Preparation of the Blocking Group

Step 1:

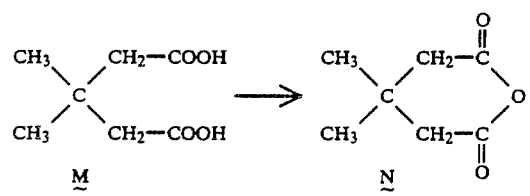

A two-liter flask is charged with compound M (100 g, 0.62 m) dissolved in one liter of dichloromethane. Acetyl chloride (50 ml, 0.7 m) is added and the resulting mixture is stirred at room temperature for an overnight period (about 16 hours). The solution is then poured into a large excess of crushed ice in a beaker. The organic phase is separated, washed with water and dried over sodium sulfate. The solvent is removed under reduced pressure to yield a white solid, 86 g, m.p. 120°–122° C., compound N.

Anal. Calcd. for $C_7H_{10}O_3$: C, 59.1; H, 7.1. Found: C, 59.4; H, 7.8.

Step 2:

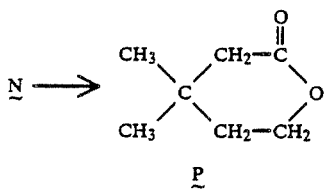

A nitrogen atmosphere is maintained in a 500 ml flask containing a solution of sodium borohydride (1.9 g, 0.05 m) in 30 ml of dry tetrahydrofuran. Compound N (7.1 g, 0.05 m), dissolved in 70 ml of dry tetrahydrofuran is added dropwise at such a rate that the temperature does not exceed 5° C. The reaction mixture is stirred at ambient temperature, then heated to reflux for 1.5 hours, and stirred for 16 hours.

Concentrated hydrochloric acid is added dropwise until a pH of 1 is reached. Water (100 ml) is then added and the product is extracted with ether. The ether extracts are dried over sodium sulfate and removed under reduced pressure to yield a colorless oil, 6.8 g, compound P.

Step 3:

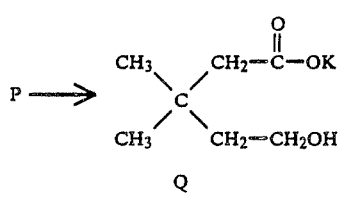

Compound P (12.8 g, 0.1 m) is dissolved in 130 ml of ethanol and a solution of potassium hydroxide (5.6 g, 0.11 m) in 10 ml of water is added. The solution is heated with steam for three hours and the ethanol and water are removed under reduced pressure. Toluene (50 ml) is added and the remaining water is removed by azeotropic distillation. The toluene is decanted from the solid mass, the solid is collected, washed with hexane and dried in a vacuum oven for 16 hours; then used directly in the next step.

Step 4:

$Q + ClCH_2O-CH_2-CH(CH_3)_2 \longrightarrow$

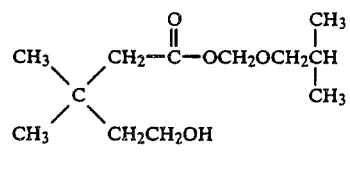

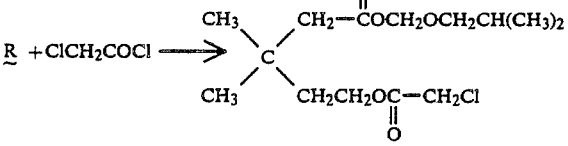

Compound Q (9.2 g, 0.05 m) is dissolved in 180 ml of dry N,N-dimethylformamide. Chloromethylisobutyl ether (6.7 g, 0.055 m) is added and a white precipitate begins to form. The mixture is stirred an additional hour at room temperature and then the temperature is lowered to 0° C. Chloroacetyl chloride (4.4 ml, 0.055 m) is added, followed by pyridine (4.0 ml, 0.05 m). The mixture is stirred at ambient temperature for an additional hour. The mixture is poured onto ice and hydrochloric acid and extracted with ethyl acetate. The extracts are dried over sodium sulfate and the solvent is removed under reduced pressure (a vacuum pump is used to remove the last trace of N,N-dimethylformamide). There is obtained 13.9 g of compound S.

Step 5:

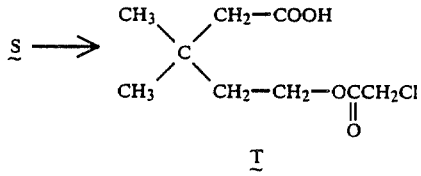

Step 5:

T → 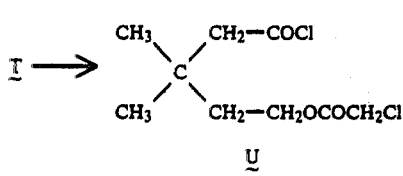

U

Compound S (2.3 g, 0.008 m) in a mixture of 5 ml of formic acid, 5 ml of water and 5 ml of tetrahydrofuran is stirred at room temperature for 16 hours. The mixture is poured into ice water and extracted with ethyl acetate. The extracts are washed with water, dried over sodium sulfate and removed under reduced pressure to give compound T.

Compound T (1.67 g, 0.0075 m) is dissolved in 25 ml of dry dichloromethane and the solution is cooled to 0° C. Oxalyl chloride (3.2 ml, 0.0375 m) is added and the reaction mixture is stirred at ambient temperature for two hours. The solvent is removed under reduced pressure, a fresh portion of dichloromethane is added and removed in the same manner. The blocking group, compound U is obtained as an oil.

Part 2: Preparation of the Carrier

Step 1:

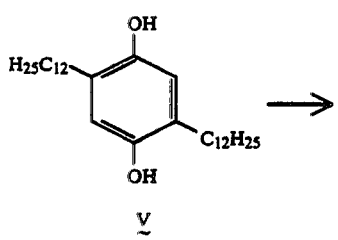

V

→

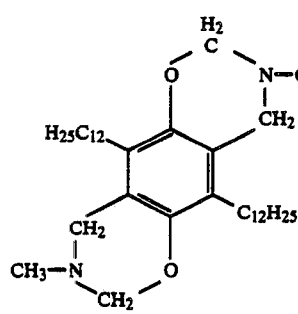

W

A 22-liter flask is charged with butanol (8.6 kg), methylamine (1 kg, 32 m), formaldehyde (2.2 kg, 37% solution in water) and Compound V (2 kg, 4.6 m). This mixture is stirred and refluxed until all the water is removed by azeotropic distillation. The hot reaction mixture is poured into 5 gallons of cold acetone, stirred well and the solvent is removed by suction. The solid is triturated with acetone, collected and washed with acetone, then vacuum dried at 50° C. under nitrogen. There is obtained 1879 g of compound W.

Step 2:

W → 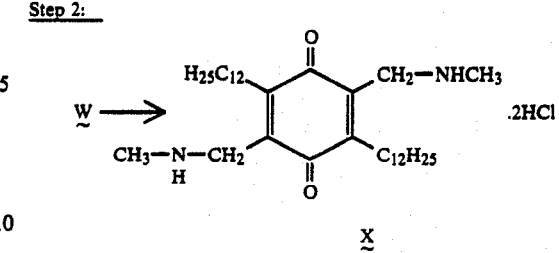

X

Compound W (1320 g, 2.4 m) is slurried in 10 liters of methanol and treated with concentrated hydrochloric acid (2260 ml) and a solution of ferric chloride (1410 g, 6.2 m) in 11 liters of water. The solution is boiled for one hour, cooled and the yellow solid is collected and washed with water. Recrystallization from alcohol yields 1000 g of compound X.

Step 3:

X → 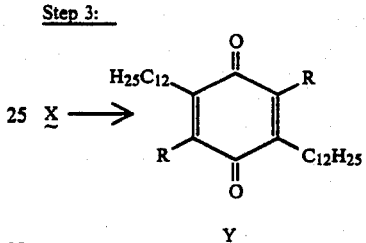

Y

R = 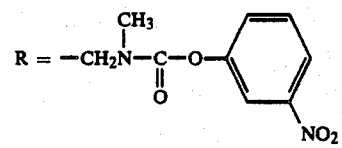

Compound X (102 g, 0.17 m) is slurried in 2.5 liters of dichloromethane and treated while being cooled with diisopropylethylamine (104 g, 0.8 m) in 100 ml of dichloromethane, followed by m-nitrophenylchloroformate (81 g, 0.4 m) in 200 ml of dichloromethane. The mixture is then acidified with 1 liter of 2 N hydrochloric acid, the organic layer is separated and washed with water. The organic layer is separated, dried over magnesium sulfate and concentrated under reduced pressure to an oil. The oil is recrystallized from 600 ml of acetonitrile, chilling to precipitate the solid. The solid material is collected, washed with cold acetonitrile to yield 138 g, m.p. 111°–112° C. of compound Y.

Step 4:

Y → 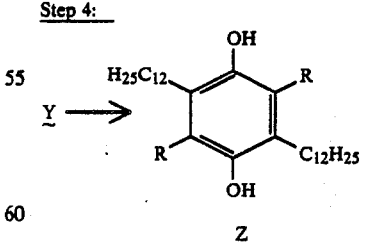

Z

R = 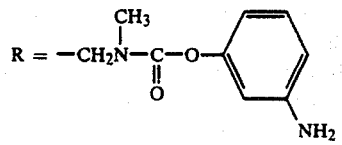

Compound Y (373 g, 0.43 m) in 8 liters of tetrahydrofuran is treated with platinum oxide (3 g) and shaken in a 5 gallon reactor under 80–90 pounds of hydrogen at 50° C. for 24 hours. The catalyst is filtered off, the solvent is removed under reduced pressure and the residue is triturated with ethyl acetate. There is obtained 310 g, m.p. 179°–181° C. of compound Z.

Step 5:

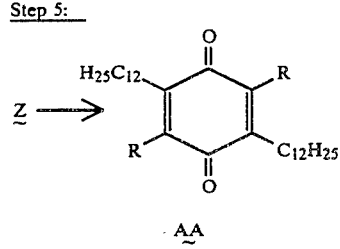

AA

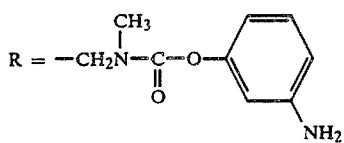

Compound Z (310 g, 0139 m) is slurried in 6 liters of dichloromethane with lead oxide (775 g, 3.2 m) for one hour at room temperature. The lead is filtered off and washed well with dichloromethane, the washings are returned to the reaction mixture, the solvent is removed under reduced pressure and the resulting solid is recrystallized from 600 ml of toluene and 1800 ml of hexane. There is obtained 258.5 g, m.p. 81°–83° C. of compound AA.

Part 3 Attachment of the Carrier to the Dye

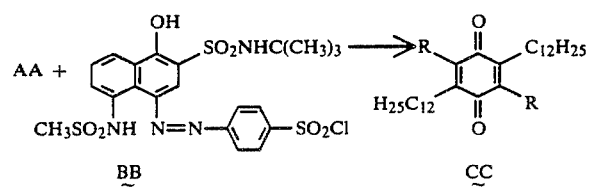

-continued

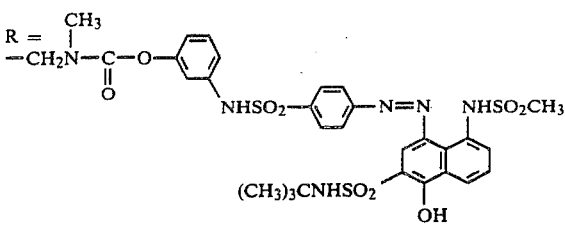

Compound AA (8.01 g, 0.01 m) is dissolved in 100 ml of dry pyridine and compound BB (17.25 g, 0.03 m) is added. After 1.5 hours, thin-layer chromatography shows that the reaction is incomplete. An additional 10% quantity of compound BB is added. After two additional hours, the reaction mixture is poured onto ice and hydrochloric acid. The mixture is extracted with ethyl acetate, the solvent is dried over magnesium sulfate and removed under reduced pressure. The material is chromatographed on silica gel using 2.5% methanol in ethyl acetate as eluent. The large magenta band is collected and the solvent removed under reduced pressure to give 8 g of compound CC.

Part 4 Attachment of the Blocking Group to the Dye

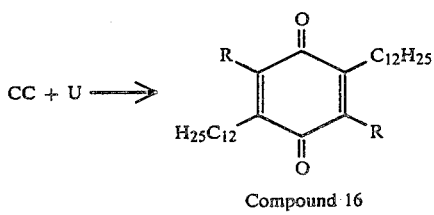

Compound 16

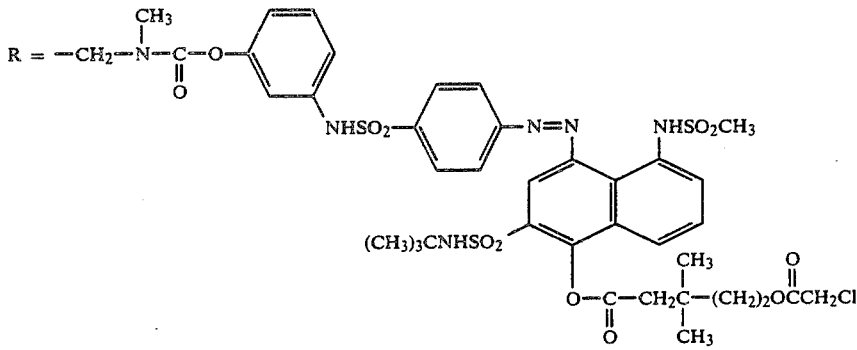

Compound CC (1.88 g, 0.001 m) is dissolved in 300 ml of dry acetone. To this solution is added diisopropylethyl amine (0.25 g, 0.002 m) and blocking group U (1.2 g, 0.005 m). Pyridine (0.4 g, 0.005 m) is diluted with 10 ml of dry acetone and this solution is added dropwise. After four hours, thin-layer chromatographic analysis indicates that the reaction is complete.

The reaction mixture is poured onto ice and hydrochloric acid (100 ml) and extracted with several 50 ml-portions of ethyl acetate. The extracts are combined, dried over sodium sulfate and concentrated under reduced pressure. The resulting oil is chromatographed on 300 g of silica gel using 5% tetrahydrofuran in dichloromethane as eluent. The large, deep orange band is collected and the solvent is removed under reduced pressure. The residue is precipitated from ligroin to give 750 mg of compound 16.

Example 4—Preparation of Compound 26

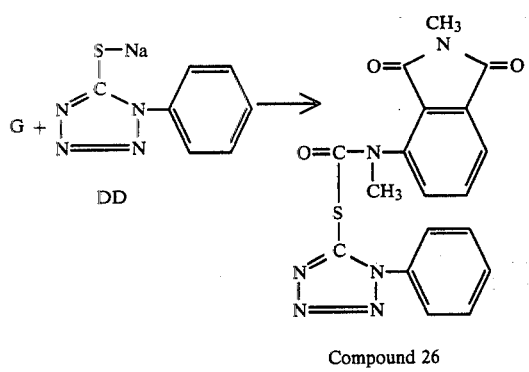

Compound 26

To a stirred solution of compound DD (6 g, 0.03 m) in 50 ml of dry ethyl acetate is added a solution of blocking group G from Example 2 (6.5 g, 0.026 m) in 50 ml of dry ethyl acetate. The solution is stirred at ambient temperature for 16 hours. The white product is filtered off, added to 500 ml dry tetrahydrofuran and stirred for one hour. The insoluble sodium chloride is removed by filtration and the filtrate is concentrated under reduced pressure to a white solid. Trituration with hexane yields 7.5 g, of white product, compound 26, m.p. 177°–178° C. Anal. Calcd. for $C_{18}H_{14}N_6O_3S$: C, 54.8; H, 3.6; N, 21.3; S, 8.1. Found: C, 55.0; H, 3.5; N, 21.3; S, 8.4.

Example 5—Preparation of Compound 39

Part 1 Preparation of the Blocking Group

Step 1:

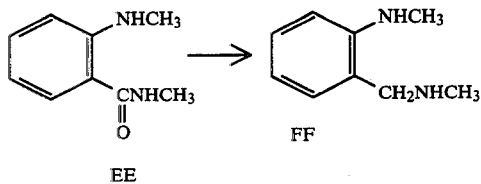

Nine liters of dry toluene are placed in a 22-liter flask, cooled by a dry ice-acetone bath. Under a nitrogen atmosphere, 3.3 liters (12.6 m) of 70% sodium bis(2-methoxyethoxy) aluminum hydride in benzene, is added over 15 minutes at a temperature of 15°–20° C. A solution of compound EE (6.84 g, 4.17 m) in 3 liters of dry tetrahydrofuran is then added over one hour at 15°–20° C. The reaction mixture is stirred for an additional 30 minutes at 15°–20° C. and then heated at reflux under nitrogen for 16 hours.

The mixture is hydrolyzed by the slow addition of 594 ml of tetrahydrofuran and 522 ml of water, keeping the temperature at 15°–20° C. The organic layer is separated, washed twice with water, dried and the solvent removed under reduced pressure. The residue is then distilled at 115°–120° C. (10 mm) to yield 442 g of compound FF.

Step 2:

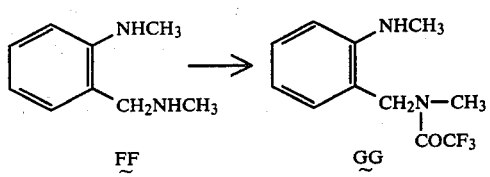

Compound FF (69 g, 0.46 m) and ethyltrifluoroacetate (65.3 g, 0.46 m) are dissolved in tetrahydrofuran and the solution is refluxed for three hours. The mixture is concentrated to dryness under reduced pressure. The residue is dissolved in dichloromethane, then washed twice with 1% acetic acid in water (200 ml); the solvent is separated, dried and removed under reduced pressure to yield compound GG, as an oil, that is used directly in the next step.

Step 3:

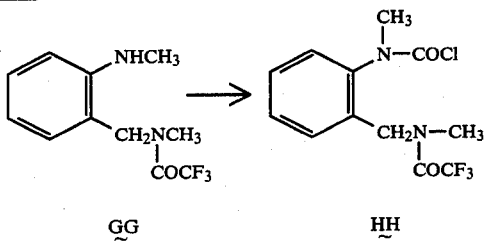

Phosgene gas is bubbled into 1 liter of dichloromethane in a 3-liter flask until 250 g is absorbed (30 minutes at 5° C.). A solution of triethylamine (63 ml, 0.44 m) and compound GG (110 g, 0.447 m) in dichloromethane is added slowly at 12° C. Triethylamine hydrochloride sublimes in the flask. After setting for about 64 hours, the triethylamine hydrochloride is removed by filtration and the filtrate is washed with water, dried over sodium sulfate and concentrated under reduced pressure (at 40° C.) to an oil.

The oil is dissolved in two parts of ethyl ether and two parts of hexane is added. After cooling in a dry ice-acetone bath, a solid mass is obtained. More hexane is added and the mixture is stirred to give a fine crystalline solid. The solid is collected, washed with hexane and dried to yield 134 g of the blocking group, compound HH, m.p. 52°–54° C.

Part 2 Attachment of the Blocking Group to the Electron Transfer Agent

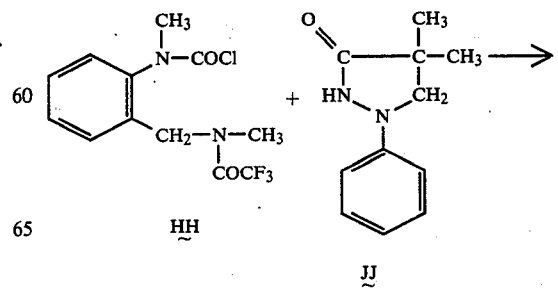

-continued

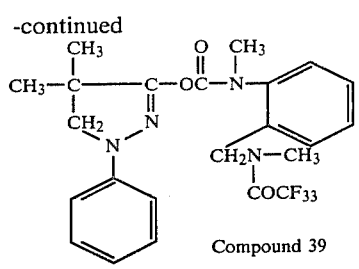

Compound 39

Compound JJ (1.90 g, 0.01 m) is dissolved in 40 ml of N,N-dimethylacetamide and treated with potassium tert-butoxide (1.23 g, 0.011 m). When the solution is homogeneous, it is cooled to 0° C. and treated with compound HH (3.08 g, 0.01 m) in 20 ml of N,N-dimethylacetamide. After stirring at 0° C. for 1 hour, the solution is stirred for 16 hours at ambient temperature. The solution is then poured into water and extracted with ethyl acetate; the extracts are separated, washed with water and brine, dried and concentrated under reduced pressure to yield a yellow oil. Chromatography on silica gel yields 3.42 g of compound 31 as a pale brown oil.

Example 6—Preparation of Compound 92

Part 1 Preparation of the Blocking Group

Step 1:

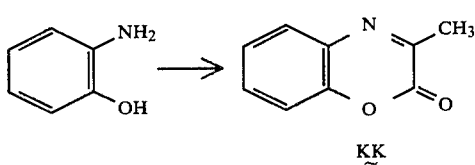

KK

Methylpyruvate (13.99 g, 0.137 m), dissolved in methanol is added to a methanol solution of o-aminophenol (14.95 g, 0.137 m) and the resulting solution is refluxed under a nitrogen atmosphere for 30 minutes. After setting for 16 hours, decolorizing carbon is added and the mixture is filtered. The filtrate is concentrated under reduced pressure to yield an orange solid. The solid is recrystallized from 50 ml of methanol to give orange crystals. After drying at 40° C. under vacuum, there is obtained 8.4 g of compound KK, m.p. 98.5°–99° C.

Step 2:

KK →
LL

Compound KK (2.1 g, 0.013 m) is dissolved in 150–200 ml of ethyl acetate, treated with palladium on carbon catalyst (0.5 g) and shaken under a hydrogen atmosphere at 80° C. for six hours. After cooling, the catalyst is removed by filtration and the filtrate is concentrated under reduced pressure. Treatment of the residue with hexane gives colorless crystals of compound LL (1.4 g, m.p. 103°–104° C.).

Step 3:

LL →
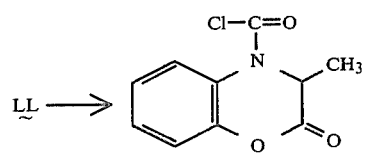
MM

A solution of phosgene in toluene (12%, 70 ml, 0.07 m) is dissolved in 40 ml of dry tetrahydrofuran and the solution is stirred and cooled to −70° C. under a nitrogen atmosphere. Compound LL (1.6 g, 0.01 m) and diisopropylethylamine (2.6 g, 0.02 m) are dissolved in 10 ml of dry tetrahydrofuran and added over a five-minute period. A white precipitate is formed after the addition. The reaction mixture is stirred at −70° C. for 30 minutes, then allowed to warm to room temperature. The solvent is removed under reduced pressure, the residue is dissolved in 100 ml of methylene chloride, washed with water (20 ml) and dried over sodium sulfate. The drying agent is removed by filtration and the filtrate concentrated under reduced pressure to yield 2 g of the blocking group, compound MM, which is used directly in the next step.

Part 2 Attachment of the Blocking Group to the Coupler

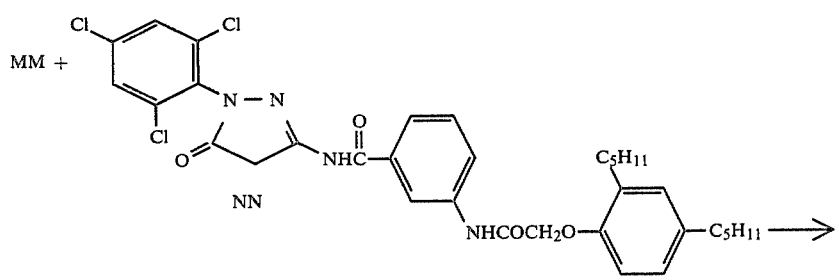

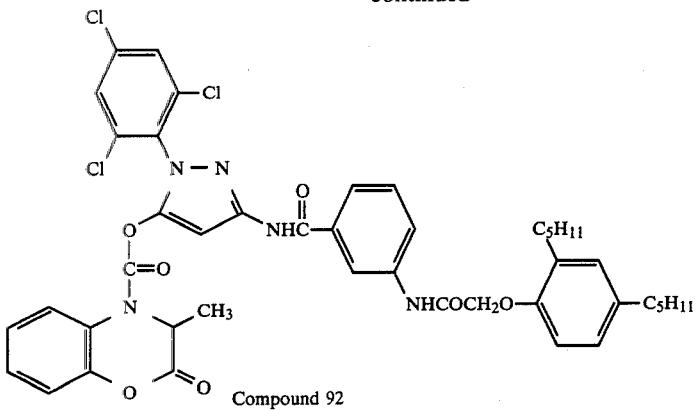

Compound 92

Compound MM (2 g, 0.009 m), dissolved in 20 ml of dry tetrahydrofuran is added to coupler NN (5 g, 0.0075 m), dissolved in 60 ml of dry pyridine and 60 ml of dry tetrahydrofuran. The reaction mixture is stirred for 2 hours and 15 minutes and then poured into a mixture of 60 ml of hydrochloric acid, 100 ml of water and 200 g of ice. The mixture is stirred thoroughly, extracted with ethyl actate (2×150 ml), the extracts are dried over sodium sulfate and the solvent removed under reduced pressure to yield the crude product. This material is chromatographed on silica gel using ethyl acetate-hexane (2:1) as eluent. After removal of the solvent there is obtained 2.1 g of compound 92, m.p. 135°–140° C. Anal. Calcd. for $C_{44}H_{44}Cl_3N_5O_7$: C, 61.4; H, 5.1; Cl, 8.1; N, 12.4. Found: C, 61.4; H, 5.6; Cl, 8.1; N, 12.6.

EXAMPLE 7—Preparation of Compound 69

2-N-Methyl-N-[o-(formyloxymethyl)phenyl]carbamoyl-1-phenyl-3-pyrazolidinone

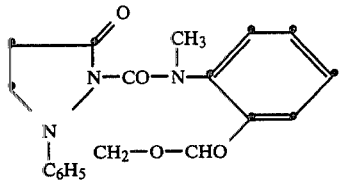

Step 1: 2-Chloroformyl-1-phenyl-3-pyrazolidinone

To a rapidly mechanically stirred—78° C. solution of dichloromethane (250 ml), containing a 1 N toluene solution of phosgene (204 ml-0.204 mole), and protected by a nitrogen atmosphere, was added a solution of 1-phenyl-3-pyrazolidinone and diisopropylethylamine in 200 ml of a 1:1 mixture of dimethylacetamide (DMA) and dichloromethane [prepared by dissolving 30.0 g(0.185 mole)1-phenyl-3-pyrazolidone in 100 ml of DMA and adding next the dichloromethane and then the diisopropylethylamine (35.5 ml, 0.204 mole]. The addition was rapid but dropwise, requiring≈30 minutes; a precipitate began to appear about 2/3 through the addition. After 10 minutes additional stirring at −78° C., the reaction was quenched by adding 6 ml of concentrated HCl. The reaction was then added to 500 ml of cold 1 N HCL and 500 ml of dichloromethane. After brief shaking the layers were separated and the dichloromethane layer briefly washed with 500 ml of cold 1 N HCl. After drying over anhydrous MgSO4, the solution was concentrated in vacuo to approximately 300 ml and the precipitate which had appeared was collected and washed with ligroin. After drying in vacuo overnight the yield of this white solid was 34.7 g (83%).

Step 2:
2-N-Methyl-N-(o-hydroxymethylphenyl)carbamoyl-1-phenyl-3-pyrazolidinone

To a solution of o-methylaminobenzyl alcohol (30.5 g, 0.22 mole) and 2,6-lutidine (23.8 g, 0.22 mole) in dichloromethane (450 ml), cooled to 0° C. and protected by a drying tube, was added 2-chloroformyl-1-phenyl-3-pyrazolidinone (50.0 g, 0.22 mole) in portions over about 5 minutes. The reaction mixture was stirred an additional 5 minutes and was then added to cold 1 N HCl. After separating the layers, the aqueous phase was extracted once with dichloromethane. The combined organic solution was washed with cold 1 N HCl and brine, dried over anhydrous MgSO4, and concentrated in vacuo to give a thick oil. This crude oil was used for the formylation step.

Step 3:
2-N-Methyl-N-(o-hydroxymethylphenyl)carbamoyl-1-phenyl-2-pyrazolidinone (72.4 g, 0.22 mole) was dissolved in 500 ml tetrahydrofuran and cooled to 0° C. Separately, formic acid (60 ml) was added to acetic anhydride (120 ml) with cooling and stirred for ½ hour. This formylating solution was then added to the pyrazolidinone solution followed by a slow addition (over about 5 minutes) of 180 ml pyridine. After 45 minutes, stirring, the mixture was diluted with 500 ml ether and added to cold 1 N HCl. After separating the layers, the aqueous phase was washed with ether. The combined ether extracts were washed with cold 1 N HCl twice and once with a brine solution. After drying over anhydrous magnesium sulfate, the ether solvent was removed in vacuo yielding an orange oil which on trituration with ether and ligroin was induced to crystallize. The solid was collected and washed with ether yielding on drying 45.6 g. The filtrate, which was observed to contain considerable acetic acid, was concentrated in vacuo, diluted with ethyl acetate, washed with cold 5% bicarbonate solution, then with acid and brine and dried as above. The yellow oil which resulted from concentration in vacuo was induced to crystallize. The solid was collected and combined with the first crop, yield 62.5 g (79%).

Example 8—Preparation of Compound 74

Hydroquinone Bis
{N-methyl-N-[2-(N-methyltrifluoroacetamidomethyl)-4-p-toluenesulfonamidophenyl]carbamate}

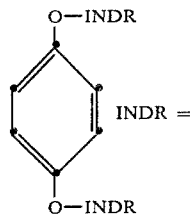

INDR =

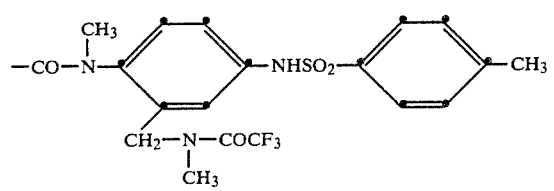

Step 1:

A solution of hydroquinone (11 g, 0.1 mole) in dichloromethane (40 ml) and tetrahydrofuran (THF) (40 ml) was added dropwise to a stirred solution of phosgene in toluene (400 ml of about 1 molar solution, approximately 0.4 mole of phosgene) maintained at −10° C. A precipitate formed which was dissolved by addition of 200 ml of THF. A solution of 2,6-lutidine (21.4 g, solution of phosgene and hydroquinone. This mixture was brought to room temperature and stirred for 48 hours. Concentration in vacuo resulted in a pale yellow solid residue. This solid was washed thoroughly with THF to dissolve the bis(chloroformate), and the extracts were concentrated again. Crystallization of the residue yielded long needles (m.p. 98°-100° C., 16.8 g, 72%) of the bis(chloroformate).

Step 2:

The bis(chloroformate) (0.5 g, 2.13 mmole) was dissolved in 5 ml of THF under a nitrogen atmosphere and cooled to 0° C. A solution of N-methyl-N-(2-methylamino-4-p-toluenesulfonamidobenzyl)trifluoroacetamide (1.77 g. 4.27 mmole) in 10 ml of THF was then added dropwise. A white precipitate formed which redissolved as a solution of N,N-diethylaniline (0.64 g, 4.27 mmole) in 5 ml of THF was added. The reaction mixture was poured into aqueous dilute HCl and extracted with dichloromethane. The organic extract was washed with brine, dried with anhydrous Na$_2$SO$_4$, and concentrated to a solid. Chromatography on silica (60:40 EtOAc: hexane) and crystallization from 2-propanol/hexane yielded 1.55 g (73%), m.p. 120 dec.

Example 9—Preparation of Compound 94

1-p-Hexanamidophenyl-4-methyl-4-(2-methyl-1,3-dioxoisoindolin-4-yl)semicarbazide

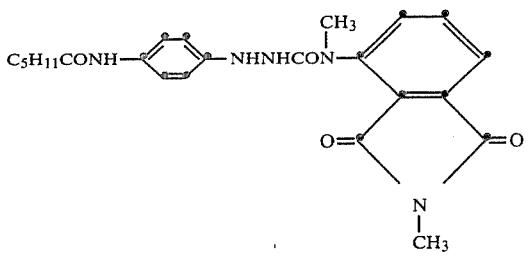

Step 1:
1-p-Nitrophenyl-4-methyl-4-(2-methyl-1,3-dioxoisoindolin-4-yl)semicarbazide p-Nitrophenylhydrazine (1.5 g, 10 mmole), N-methyl-N-(2-methyl-1,3-dioxoisoindolin-4-yl) carbamoyl chloride (2.5 g, 10 mmole) and 2 ml pyridine were combined in 25 ml dry acetonitrile, heated to reflux, then stirred at room temperature for 4 hours. The solid formed was collected and washed with ether to give 2.6 g of product, m.p. 194°-196° C.

Step 2:
1-p-Aminophenyl-4-methyl-4-(2-methyl-1,3-dioxoisoindolin-4-yl)semicarbazide 1-p-Nitrophenyl-4-methyl-4-(2-methyl-1,3-dioxoisoindolin-4-yl)semicarbazide (2.6 g) was dissolved in 300 ml tetrahydrofuran and a catalytic amount (about 200 mg) of 10% palladium on carbon was added. The mixture was hydrogenated on a Parr hydrogenation apparatus overnight at 40 psi hydrogen pressure. The mixture was filtered and the solvent was evaporated to give 2.0 g (87% yield).

Step 3
1-p-Aminophenyl-4-methyl-4-(2-methyl-1,3-dioxoisoindolin-4-yl)semicarbazide (1.5 g, 4.5 mmole) and pyridine (1 ml) were dissolved in 30 ml of acetonitrile under nitrogen and cooled to +5° C. in an ice bath. Hexanoyl chloride (0.6 g, 4.5 mmole) in 5 ml of acetonitrile was added dropwise. The mixture was stirred 1½ hours at ice-bath temperature. The resulting solid was filtered to give 0.6 g of product, m.p. 115°-118° C. Recrystallization from acetonitrile and ethyl acetate gave 0.32 g (16% yield) of product, m.p. 147°-149° C.

Example 10

Redox-dye-releasing (RDR) compounds containing blocked cyan dyes according to this invention were evaluated for (1) rate of deblocking of the dye in the dispersed phase at high pH; (2) the effect of the blocking group on rate of dye transfer through an integral-negative-receiver color transfer element and (3) the extent of deblocking under accelerated keeping conditions (raw stock incubation).

The RDR compounds were compared with RDR compounds which contained the unblocked parent of the dye and dyes containing known blocking groups.

Procedure

Color transfer elements were prepared by coating a poly(ethylene terephthalate) film support with a layer comprising the RDR compounds at $5 \times 10^{-5}$ moles/ft$^2$ ($5.4 \times 10^{-4}$ moles/m$^2$) dissolved in an organic coupler solvent and dispersed in gelatin.

A second set of coatings were prepared as above except that a silver halide emulsion (0.8μ AgBr) was also added to the RDR-containing layer at 100 mg Ag/ft$^2$ (1.1 g Ag.m$^2$).

(1) To determine the rate of deblocking, samples of the elements which did not contain the silver halide emulsion were contacted with a 1.0 N solution of sodium hydroxide (25° C.) and the amount of the unblocked dye appearing at discrete intervals was determined spectrophotometrically. Kinetic analysis of the data yields "$t_{\frac{1}{2}}$" parameters (time required to produce one-half the final density) which are recorded in Table I.

(2) To determine the effect of the blocking group on imaging and dye transfer relative to the unblocked parent RDR, samples of the elements containing the silver halide emulsion were exposed through a graduated-density step tablet and processed by rupturing a pod containing a viscous processing composition consisting of 20 g sodium hydroxide, 10 g potassium hydroxide, 25 g hydroxyethyl cellulose and 0.75 g 4-hydroxymethyl-4-methyl-1-phenyl-3-pyrazolidone in 1.0 liter water while in contact with a receiver sheet comprising a transparent support having coated thereon a dye mordant layer and a titanium dioxide reflecting layer. The rate of imagewise transfer of dye was then monitored through the receiver support by measuring the density to red light in the maximum density areas at 30, 60 and 120 seconds. The $D_{min}$ and $D_{max}$ was also measured in receiving elements which were processed as above, separated from the corresponding photosensitive elements after 1 minute, and washed.

(3) Raw stock incubation tests were performed on samples of the no-silver-containing elements which were incubated under the conditions described in Table I and compared to additional control samples that were stored in a freezer. Raw stock stability was measured as the change in density for $\lambda_{max}$ as compared to the control.

All results are recorded in Table I.

TABLE I

| RDR Compound | | Deblocking Rate $t_{\frac{1}{2}}$(sec) | Raw Stock Incubation | | | | Imaging Red Density Through Image Receiver Support | | | $D_{max}/D_{min}$ | Comments |
|---|---|---|---|---|---|---|---|---|---|---|---|
| | | | ΔD 78°/80% | | λmax 120°/50% | | | | | | |
| Number (See below for structure) | Blocking Group | | 1 wk. | 3 wks. | 1 wk. | 3 wks. | 30" | 60" | 120" | | |
| A (control) | None (H) | | Not measured | | | | 0.66 | 1.52 | 2.18 | 2.14/0.50 | — |
| B (control) | −CCH$_3$ (O) | 5.4 | 0.15 | 0.15 | 0.11 | 0.11 | 0.44 | 1.32 | 2.30 | 2.22/0.57 | Good processability; poor incubation. |
| C (control) | −COC$_2$H$_5$ (O) | 28.9 | 0.16 | 0.22 | 0.09 | 0.10 | 0.38 | 1.18 | 2.23 | 2.20/0.68 | Good processability; poor incubation. |
| D (control) | −C(O)−N(CH$_3$)−C$_6$H$_5$ | ~10,000 | 0.00 | 0.00 | 0.00 | 0.00 | 0.10 | 0.18 | 0.26 | 0.30/0.08 | Poor processability; good incubation. |
| 1 | −C(O)−N(CH$_3$)−⟨cyclohexyl−CH$_2$OCCH$_2$Cl(O)⟩ | 3 | 0.00 | 0.00 | 0.00 | 0.00 | 0.53 | 1.56 | 2.22 | 2.20/0.46 | Good processability; good incubation |
| 2 | −C(O)−N(φ)−(CH$_2$)$_2$OCCCl$_3$(O) | 25 | 0.00 | 0.00 | 0.00 | 0.00 | 0.40 | 1.40 | 2.20 | 2.20/0.60 | Good processability; good incubation. |
| 3 | −C(O)−N(CH$_3$)−⟨cyclohexyl−CH$_2$−O−C(O)⟩ | 28 | 0.00 | 0.00 | 0.01 | 0.02 | 0.32 | 0.84 | 1.74 | 2.02/0.46 | Good processability; good incubation |
| 4 | −C(O)−N(C$_2$H$_5$)−⟨cyclohexyl−CH$_2$−O−C(O)⟩ | 28 | 0.00 | 0.00 | 0.00 | 0.00 | 0.28 | 1.06 | 2.00 | 2.01/0.48 | Good processability; good incubation |

TABLE I-continued

| RDR Compound | | Deblocking Rate $t_{\frac{1}{2}}$(sec) | Raw Stock Incubation | | | | Imaging Red Density Through Image Receiver Support | | | $D_{max}/D_{min}$ | Comments |
| --- | --- | --- | --- | --- | --- | --- | --- | --- | --- | --- | --- |
| Number (See below for structure) | Blocking Group | | ΔD 78°/80% | | λmax 120°/50% | | | | | | |
| | | | 1 wk. | 3 wks. | 1 wk. | 3 wks. | 30" | 60" | 120" | | |
| 5 | ![structure with CH₂N-CCF₃, CH₃, -C(=O)-N-cyclohexyl] | 25 | 0.00 | 0.00 | 0.02 | 0.02 | 0.30 | 0.88 | 1.78 | 2.08/0.58 | Good processability; good incubation |

Structure (for Table I):

OH
naphthalene-CONH(CH₂)₄O-phenyl(C₅H₁₁-t)(C₅H₁₁-t)
NHSO₂-phenyl-SO₂NH-naphthalene(O—Blocking Group)-N=N-phenyl(SO₂CH₃)(NO₂)

Example 11

Redox-dye-releasing compounds containing blocked magenta dyes according to this invention were evaluated as described in Example 10. The results are recorded in Table II.

Example 12

Single layer elements containing positive-working dye releasing compounds were prepared having the following structure. Amounts of components are shown in parentheses.

TABLE II

| RDR Compound | | Deblocking Rate $t_{\frac{1}{2}}$(sec) | Raw Stock Incubation | | | | Imaging Red Density Through Image Receiver Support | | | $D_{max}/D_{min}$ | Comments |
| --- | --- | --- | --- | --- | --- | --- | --- | --- | --- | --- | --- |
| Number (See below for structure) | Blocking Group | | ΔD 78°/80% | | λmax 120°/50% | | | | | | |
| | | | 1 wk. | 3 wks. | 1 wk. | 3 wks. | 30" | 60" | 120" | | |
| E (Control) | —COC₂H₅ | 31 | 0.09 | 0.13 | 0.14 | 0.18 | 0.31 | 0.94 | 1.60 | 2.20/0.48 | Good processability; poor incubation |
| F (Control) | —C(O)—N(C₆H₅)₂ | >300 | 0.00 | 0.01 | 0.00 | 0.01 | 0.16 | 0.17 | 0.20 | very poor image | Poor processability; good incubation |
| 7 | —C(O)—N(C₂H₅)-cyclohexyl-CH₂-O- | 82 | 0.00 | 0.00 | 0.00 | 0.00 | 0.14 | 0.68 | 1.58 | 1.40/0.30 | Good processability |
| 8 | (same bicyclic structure with C=O) | 107 | 0.00 | 0.00 | 0.00 | 0.00 | 0.23 | 0.83 | 1.72 | 1.52/0.37 | Good incubation |

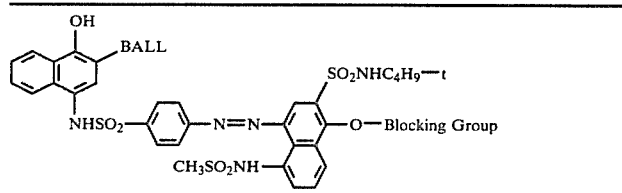

Structure:
OH, BALL on naphthalene, SO₂NHC₄H₉-t, NHSO₂-phenyl-N=N-, O—Blocking Group, CH₃SO₂NH Ball is: For RDR Compounds E, F and 7 —CONH(CH₂)₄—O—phenyl(C₅H₁₁-t)(C₅H₁₁-t)

For RDR Compound 8 —CON(C₁₂H₂₅—n)₂.

| | |
|---|---|
| Gelatin Overcoat | (0.54 g/m$^2$) |
| Silver bromide as silver | (1.08 g/m$^2$) |
| Dye releasing compound | (see Table) |
| Electron Donor | (7.56 × 10$^{-4}$ mol/m$^2$) |
| Coupler solvent (equal to combined weight of dye releasing compound and reducing agent) | |
| Gelatin | (2.16 g/m$^2$) |
| Polyethylene Terephthalate Support | |

With elements containing positive-working dye releasing compounds, the best $D_{max}$ and the fastest rate of release are obtained if no silver halide is developed This condition can be obtained by fixing out the silver halide. Similarly, the lowest $D_{min}$ will be obtained if all the silver halide is developed. This condition can be obtained by fogging the silver halide.

The elements prepared above were treated as follows: the silver halide in one half of each element was fogged by a white light exposure and the silver halide in the other half was fixed using a conventional fixing bath. Each element was then laminated to a receiver sheet containing poly(styrene-co-N,N,N-tri-n-hexyl-N-vinylbenzyl ammonium chloride) on a poly(ethyleneterephthalate) support, with the following processing composition between the element and the receiver:

| Processing Composition | |
|---|---|
| Potassium hydroxide | 51 g/l |
| 1-Phenyl-4-methyl-4-hydroxymethyl-3-pyrazolidone | 3 g/l |
| Carboxymethyl cellulose | 40 g/l |

The film strips were cut into five strips which were sequentially peeled apart and washed 1, 3, 5, 10 and 20 minutes after lamination. The dye density of the unblocked dye in the fixed half of each strip was measured and plotted versus time to give curves from which there was determined the time required to reach one-half of the maximum density. The following table lists this time as $t_{1/2}$ values for each compound and also lists values of maximum and minimum density obtained for the three-minute transfer. The $t_{1/2}$ values recorded in this table are a measure of three individual $t_{1/2}$ values: (1) unblocking of the dye; (2) release of the dye from the carrier; and (3) transfer of the dye to the receiver sheet. The value of $t_{1/2}$ for unblocking of the dye is not greater than the reported $t_{1/2}$ value and is likely smaller.

| | | | 3 Minute Transfer | |
|---|---|---|---|---|
| Compound | Amount | $T_{1/2}$ | $D_{max}$ | $D_{min}$ |
| 10 | 3.78 × 10$^{-4}$ mol/m$^2$ | 180 | 0.6 | 0.01 |
| 12 | 1.89 × 10$^{-4}$ mol/m$^2$ | 50 | 1.05 | 0.000 |
| 13 | 1.89 × 10$^{-4}$ mol/m$^2$ | 40 | 1.11 | 0.00 |
| 15 | 1.89 × 10$^{-4}$ mol/m$^2$ | 180 | 0.59 | 0.01 |
| 16 | 1.89 × 10$^{-4}$ mol/m$^2$ | 45 | 0.72 | 0.08 |

These results indicate that the dye is unblocking at a satisfactory rate.

Example 13

Development inhibitors, electron transfer agents and couplers, blocked in accordance with this invention were tested to determine rate of unblocking by dissolving the compound in a mixed solvent system composed of 50% acetonitrile and 50% aqueous potassium phosphate buffer (pH about 12). The concentration of the compound to be tested was about 1 × 10$^{-4}$ molar. The release of the blocking group was followed spectrally and plotted as a function of time. From the curves obtained unblocking rate and $t_{1/2}$ are calculated. The results are reported below.

| Compound | pH | Rate of Unblocking (Sec$^{-1}$) | $t_{1/2}$ of Unblocking (Sec) |
|---|---|---|---|
| 23 | 12 | 6.6 × 10$^{-3}$ | 105 |
| 26 | 12 | 7.8 × 10$^{-3}$ | 88 |
| 42 | 12 | 2.6 × 10$^{-3}$ | 266 |
| 92 | 11.62 | 2.87 × 10$^{-1}$ | 2.4 |

Satisfactory rates of unblocking were obtained at pH 12. At pH 14 the $t_{1/2}$ for unblocking would be approximately two order of magnitude faster.

Example 14

The unblocking rates of pyrazolidinone developing agents and 1-phenyl-2-tetrazolin-5-thione development inhibitors were measured as in Example 13. The blocked compounds were dissolved in acetonitrile to which an equal volume of 1 N NaOH was added to give a mixed solvent "pH" of about 13 and a concentration of blocked compound of 1 × 10$^{-4}$ molar. The release of the blocking group was followed spectrally and calculated as in Example 13. The $t_{1/2}$ values are given below.

| Compounds | $t_{1/2}$ (sec) |
|---|---|
| 24 | 80 |
| 29 | 330 |
| 44 | 300 |
| 45 | 80 |
| 46 | 395 |
| 47 | 385 |
| 48 | 370 |
| 49 | 35 |
| 50 | 100* |
| 52 | 135 |
| 53 | 31 |
| 56 | 84 |
| 57 | 93 |
| 66 | 37 |

*Dioxane was used in place of acetonitrile to enhance solubility.

Example 15

Elements were prepared having the following structure. Coverages are in grams per square meter.

| | |
|---|---|
| Gelatin | 0.54 |
| Cyan dye releasing compound | 0.38 |
| Electron transfer agent A or Blocked electron transfer agent Compound No. 32 | 0.17 |
| | 0.37 |
| Gelatin | |
| Red-sensitive direct positive silver halide as Ag | 1.08 |
| Gelatin | |
| Support | |

The dye releasing compound had the structure:

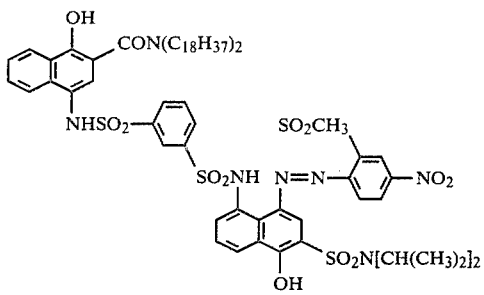

Electron transfer agent A was p-methylaminophenol.

The fresh elements were cut in half and one half of each element was exposed for 1/100 second through a graduated density test object and laminated to a receiving sheet comprising a carbon layer, a reflecting layer and a mordant layer on a film support with a processing composition containing potassium hydroxide, carboxymethylcellulose and potassium fluoride between the element and the receiver. After one minute the image was viewed through the clear support and good image discrimination was obtained in each element. The other half of each element was kept at ambient conditions for several days and then processed as described above. The element containing electron transfer agent A gave no image discrimination whereas the element containing blocked electron transfer agent 32 of this invention gave acceptable image discrimination.

Example 16

A multilayer multicolor image transfer film unit was prepared having the following schematic structure. Amounts of the components are given in grams/square meter.

| |
|---|
| Clear polyester support |
| Neutralizing layer |
| Timing Layer |
| Pod With Processing Composition (see below) |
| Gelatin |
| Blue-sensitive negative-working silver halide, as silver - 1.62; Yellow dye releasing compound (see below) - 0.41; Electron Donor - 0.41; Development inhibitor releasing compound - 0.007; Coupler solvent - 0.41; Gelatin - 2.16 |
| Gelatin - 1.02; Scavenger for electron transfer agent - 0.43; Filter Dye - 0.65 |
| Green sensitive negative working silver halide, as silver - 1.35; Magenta dye releasing compound No. 12 - 0.48; Electron donor - 0.35; Development inhibitor releasing compound - 0.007; Coupler solvent - 0.82; Gelatin - 1.34 |
| Gelatin - 1.02; Scavenger for electron transfer agent - 0.43; Filter dye - 0.65 |
| Red sensitive negative working silver halide as silver - 1.35; Cyan dye releasing compound No. 11 - 0.31; Electron donor - 0.25; Development inhibitor releasing compound - 0.007; Coupler solvent - 0.28; Gelatin - 1.24 |
| Gelatin |
| Opaque Layer |
| Light Reflecting Layer |
| Receiving Layer |
| Clear Polyester Support |

The processing composition was contained in a pressure rupturable pod in the location shown. It had the following composition:

| | |
|---|---|
| 4-hydroxymethyl-4-methyl-1-phenyl-3-pyrazolidone | 12 g/l |
| potassium bromide | 5 g/l |
| potassium hydroxide | 51 g/l |
| sodium ethylenediaminetetra-acetic acid | 10 g/l |
| sodium sulfite | 2 g/l |
| carboxymethyl cellulose | 833 g/l |
| carbon | 42 g/l |
| water to | 1 liter |

The yellow dye releasing compound had the structure:

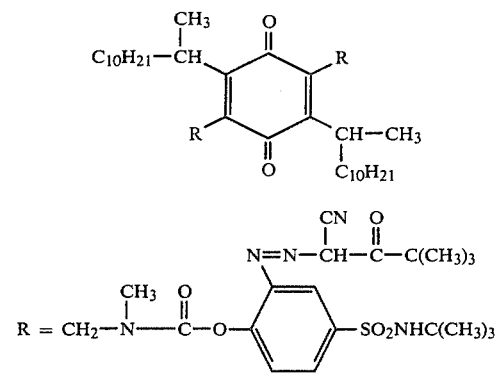

The element was imagewise exposed for 1/50 of a second through a multicolor graduated density test object and prepared by rupturing the pod containing the processing composition. Maximum density was allowed to develop in the element, yielding a well defined positive reproduction of the test object. Maximum and minimum density values were as follows:

| | $D_{max}$ | $D_{min}$ |
|---|---|---|
| Blue | 2.26 | 0.24 |
| Green | 1.86 | 0.19 |
| Red | 1.86 | 0.26 |

Example 17—Incorporated Blocked Pyrazolidinone Developing Agents in a Multicolor Transfer Imaging Element A multilayer tricolor image transfer photosensitive element was prepared by coating the following layers on an opaque polyester support. Units are (g/m$^2$) or [mg/mole Ag].

| | |
|---|---|
| Layers 1 and 2 | A neutralizing layer (1) and timing layer (2), respectively, with adhesive layers between layers 1 and 2. |
| 3 | A cyan dye-releaser (see below), (0.41) in coupler solvent (0.20) dispersed in gelatin (1.56) and potassium 5-octadecylhydroquinone-2-sulfonate (0.048) |
| 4 | A 0.6 μm red-sensitized silver chloride emulsion (0.32 Ag, 0.62 gel) + a phenylmercaptotetrazole (PMT) antifoggant. |
| 5 | A gelatin (1.23) interlayer containing a dispersion of blocked developing agent 44 (0.48) in a terpolymer latex, (0.48). |
| 6 | A magenta dye-releaser (see below) (0.45) in coupler solvent (0.22) dis- |

| | -continued |
|---|---|
| | persed in gelatin (1.02) and potassium 5-octadecylhydroquinone-2-sulfonate (0.042). |
| 7 | A 0.6 μm green-sensitized silver chloride emulsion (0.55 Ag, 0.90 gel) + octadecylquinone (0.026) + a PMT antifoggant. |
| 8 | A gelatin interlayer like layer 5. |
| 9 | A yellow dye-releaser (see below) (0.68) in coupler solvent (0.34) dispersed in gelatin (1.21) and potassium 5-octadecylhydroquinone-2-sulfonate (0.033). |
| 10 | A 0.6 μm blue-sensitized silver chloride emulsion (0.43 Ag, 0.82 gel) + octadecylquinone (0.020) + a PMT antifoggant + potassium 5-octadecylhydroquinone-2-sulfonate (0.051). |

| | -continued |
|---|---|
| 11 | A gelatin (0.89) overcoat layer + didodecylhydroquinone (0.32). |

The image receiving element employed had the following layer composition coated on a polyethylene-coated opaque paper support.

1. A gelatin (0.81) undercoat layer + formaldehyde (0.072).
2. A mordanted receiving layer containing a quaternized poly(1-vinyl-imidazole) (2.42) and gelatin (3.10).
3. A UV absorber layer containing gelatin (1.22) and a 2-phenyl benzotriazole UV absorber.
4. A gelatin (0.64) overcoat layer Compound Identification:

Cyan dye-releaser

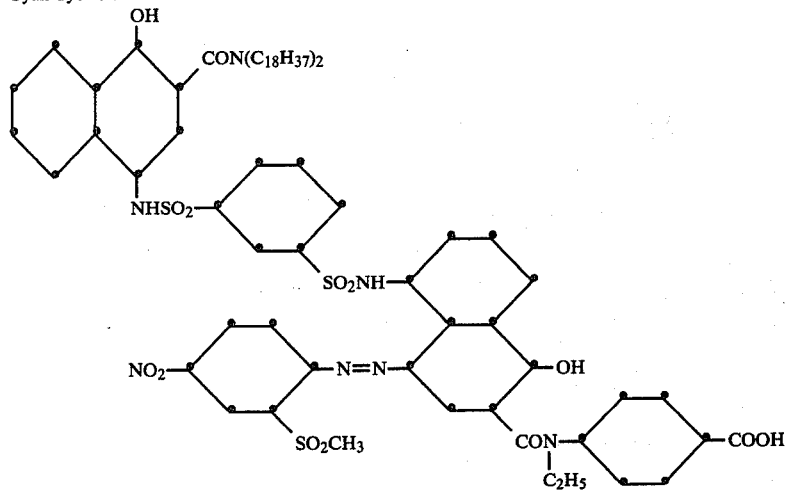

Magenta dye-releaser

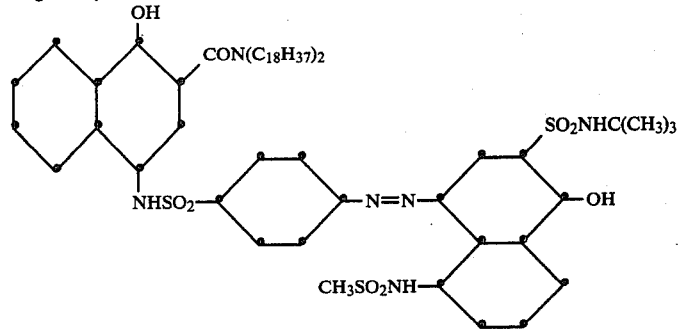

Yellow dye-releaser

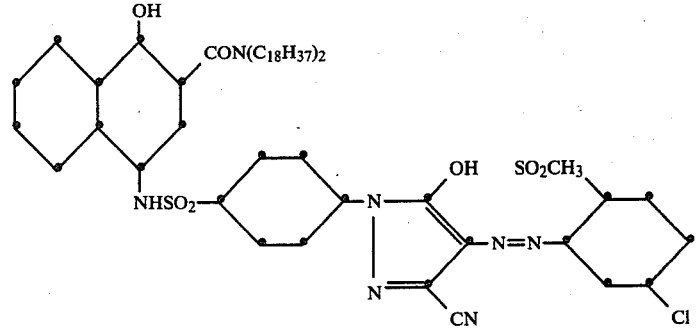

The photosensitive element was exposed in a sensitometer through a step tablet to a near-neutral light source at a Status A density of 0.8, soaked in an activator contained in a shallow-tray processor for 15 seconds at 28° C. and then laminated between nip-rollers to the dry image receiving element. After 8 minutes at 22° C., the photosensitive element and the image receiving element were separated. The Status A sensitometric curves were read from the neutral scale by reflection densitometry. The sensitometric results are reported below.

A second photosensitive element was prepared just like the first except that Compound 51 (0.32) was substituted for Compound 44 in layers 5 and 8. The sensitometric results are reported below.

The activator solution had the following composition:

| Potassium hydroxide | | | 0.6 N |
|---|---|---|---|
| 5-Methylbenzotriazole | | | 3.0 g/l |
| 11-Aminoundecanoic acid | | | 2.0 g/l |
| Potassium bromide | | | |

Sensitometry Using Blocked Pyrazolidinone Developers

| Element With Compound | | $D_{max}$ | $D_{min}$ | Relative Speed* |
|---|---|---|---|---|
| 44 | Red | 2.31 | .08 | 42 |
| | Green | 2.36 | .08 | 40 |
| | Blue | 2.14 | .08 | 40 |
| 51 | Red | 2.34 | .09 | 45 |
| | Green | 2.38 | .09 | 35 |
| | Blue | 2.12 | .09 | 42 |

*Relative speed, at D = 0.5, 10 units = 0.1 log E

Both elements showed excellent image discrimination with comparable sensitometry for the two blocked developing agents. The stability of these blocked developing agents was demonstrated by the lack of any significant change in sensitometry from that reported above after storage of the coatings for 18 months at 25° C. and 50% relative humidity.

This invention has been described in detail with particular reference to preferred embodiments thereof, but it will be understood that variations and modifications can be effected within the spirit and scope of the invention.

What is claimed is:

1. A photographic element comprising a support, at least one photosensitive silver halide emulsion layer and a blocked photographic reagent having the structure:

PR-G'-E-X-NuP where:
PR-G' is the residue of a photographic reagent, G' being oxygen, sulfur, selenium, phosphorous or nitrogen;
E is an electrophilic group;
NuP is a precursor of a nucleophilic group which, under alkaline conditions, is converted uniformly to a nucleophilic group; and
X is a linking group for spatially relating E and NuP to enable them to undergo, after conversion of NuP to a nucleophilic group, an intramolecular nucleophilic displacement reaction which cleaves the bond between E and G';
the blocked photographic reagent, under alkaline conditions encountered during processing of the silver halide emulsion layer, being uniformly unblocked, even if contacted with oxidized silver halide developing agent.

2. A photographic element of claim 1, wherein G' is oxygen, sulfur or nitrogen;
G'-E is an ester moiety or an amide moiety;
NuP is a hydrolysis sensitive ester or amide which, under alkaline conditions, is hydrolyzed uniformly to a nucleophilic group;
X is an acyclic, carbocyclic or heterocyclic linking group; and
E and NuP are joined to positions on X to form a 3- to 7-membered ring during the intramolecular nucleophilic displacement reaction between the electrophilic group and the nucleophilic group.

3. A photographic element of claim 2 wherein PR-G' is the residue of a development inhibitor, a developing agent, an electron transfer agent, a bleach inhibitor or a nucleating agent.

4. A photographic element of any one of claims 2 to 3 wherein there is associated with the silver halide emulsion layer a dye-image-providing material.

5. A photographic element of claim 4 wherein the dye-image-providing material is a dye-forming coupler.

6. A photographic element of claim 4 wherein the dye-image-providing material is a negative-working dye release compound.

7. A photographic element of claim 4 wherein the dye-image-providing material is a positive-working dye release compound.

8. A photographic element of claims 2 or 3 wherein the moiety -E-X-NuP has the structure:

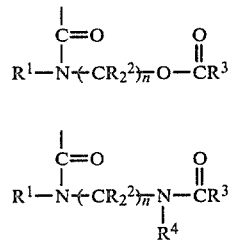

or the structure:

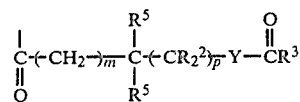

wherein:
$R^1$ is hydrogen, straight or branch chain alkyl of 1 to 20 carbon atoms or aryl of 6 to 30 carbon atoms;
Each $R^2$ is individually hydrogen or alkyl of 1 to 6 carbon atoms;
$R^3$ is hydrogen, alkyl of 1 to 20 carbon atoms or aryl of 6 to 30 carbon atoms;
$R^4$ is $R^1$;

Each $R^5$ is individually straight or branch chain alkyl of 1 to 6 carbon atoms;
n is 1 to 4;
m is 0 or 1;
p is 1 to 4; and
m+p is 1 to 4.

9. A photographic element of claims 2 or 3 wherein the moiety of -E-X-NuP has the structure

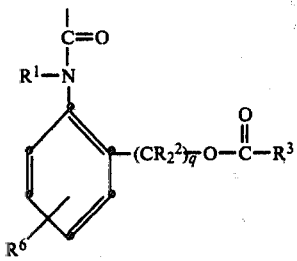

or the structure:

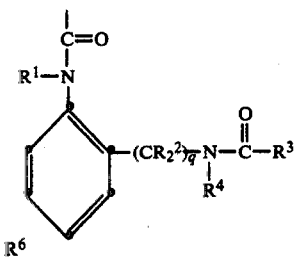

or the structure:

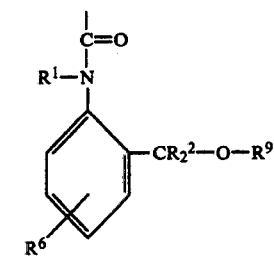

or the structure:

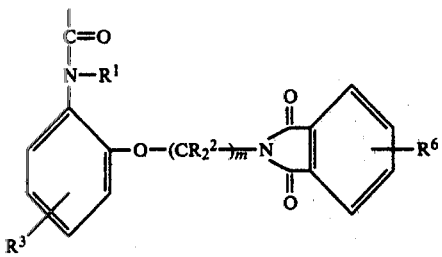

wherein:
$R^1$ is hydrogen, straight or branch chain alkyl of 1 to 20 carbon atoms or aryl of 6 1 to 30 carbon atoms;
Each $R^2$ is individually hydrogen or alkyl of 1 to 6 carbon atoms;
$R^3$ is hydrogen, alkyl of 1 to 20 carbon atoms or aryl of 6 to 30 carbon atoms;
$R^4$ is $R^1$;
q is 0 to 2;
$R^6$ is hydrogen, halogen, nitro, carboxy, straight or branch chain alkyl of 1 to 20 carbon atoms; alkoxy of 1 to 20 carbon atoms, aryl of 6 to 30 carbon atoms, alkoxycarbonyl of 2 to 20 carbon atoms; sulfamoyl having the structure —$SO_2NR^4{}_2$, sulfonamido having the structure —$NR^4SO_2R^4$, carbamoyl having the structure —$CONR^4{}_2$ or carbanamido having the structure —$NR^4COR^4$ where $R^4$ is $R^1$; and
$R^9$ is hydrogen, formyl or alkylcarbonyl.

10. A photographic element of claim 2 or 3 wherein the moiety -E-X-NuP has the structure:

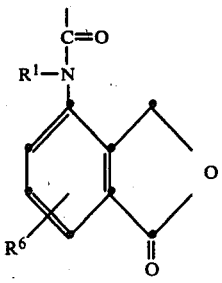

or the structure:

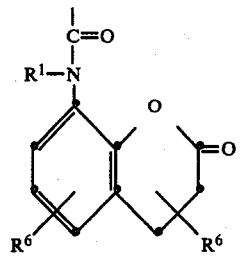

or the structure:

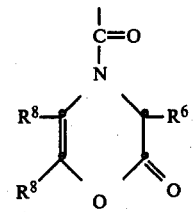

wherein:
$R^1$ is hydrogen, straight or branch chain alkyl of 1 to 20 carbon atoms or aryl of 6 to 30 carbon atoms;
$R^6$ is hydrogen, halogen, nitro, carboxy, straight or branch chain alkyl of 1 to 20 carbon atoms, alkoxy of 1 to 20 carbon atoms; aryl of 6 to 30 carbon atoms, alkoxycarbonyl of 2 to 20 carbon atoms; sulfamoyl having the structure —$SO_2NR^4{}_2$, sulfonamido having the structure —$NR^4SO_2R^4$, carbamoyl having the structure —$CONR^4{}_2$ or carbonamido having the structure —$NR^4COR^4$ where $R^4$ is $R^1$; and
each $R^8$ is $R^6$ or together both $R^8$'s form a fused aromatic ring of 5 to 6 nuclear atoms selected from carbon, nitrogen, oxygen and sulfur, which ring can be optionally substituted with one or more $R^6$ groups.

11. A photographic element of claim 2 or 3 wherein the moiety -E-X-NuP has the structure:

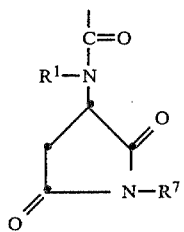

or the structure:

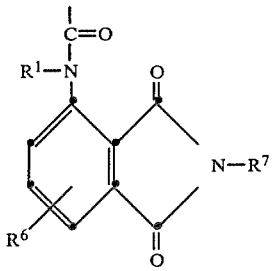

or the structure:

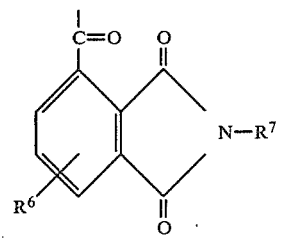

wherein:

R¹ is hydrogen, straight or branch chain alkyl of 1 to 20 carbon atoms or aryl of 6 to 30 carbon atoms;

R⁶ is hydrogen, halogen, nitro, carboxy, straight or branch chain alkyl of 1 to 20 carbon atoms; alkoxy of 1 to 20 carbon atoms, aryl of 6 to 30 carbon atoms, alkoxycarbonyl of 2 to 20 carbon atoms, sulfamoyl having the structure —SO₂NR⁴₂, sulfonamido having the structure —NR⁴SO₂R⁴, carbamoyl having the structure —CONR⁴₂ or carbonamido having the structure —NR⁴COR⁴ where R⁴ is R¹; and R⁷ is alkyl of 1 to 30 carbon atoms or aryl of 6 to 30 carbon atoms.

12. A photographic element of claim 3 wherein the blocked photographic reagent is a blocked developing agent selected from

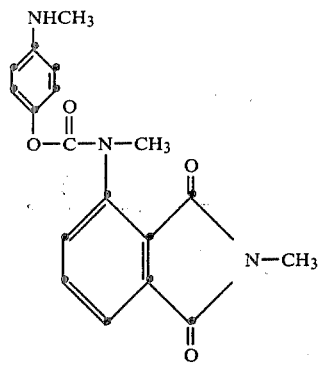

or the structure:

[structure diagram]

13. A photographic image transfer film unit for forming a dye image comprising:
(a) a photosensitive element comprising a support having thereon at least one photosensitive silver halide emulsion layer having associated therewith an immobile dye releasing compound; and
(b) a dye image-receiving layer; the film unit containing a blocked photographic reagent having the structure:

PR-G'-E-X-NuP where:
PR-G' is the residue of a photographic reagent, G' being oxygen, sulfur, selenium, phosphorous or nitrogen;
E is an electrophilic group;
NuP is a precursor of a nucleophilic group which, under alkaline conditions, is converted uniformly to a nucleophilic group; and
X is a linking group for spatially relating E and NuP to enable them to undergo, after conversion of NuP to a nucleophilic group, an intramolecular nucleophilic displacement reaction which cleaves the bond between E and G';

the blocked photographic reagent, under alkaline conditions encountered during processing of the silver halide emulsion layer, being uniformly unblocked, even if contacted with oxidized silver halide developing agent.

14. A photographic image transfer unit of claim 13 wherein

G' is oxygen, sulfur or nitrogen;

G'-E is an ester moiety or an amide moiety;

NuP is a hydrolysis sensitive ester or amide which, under alkaline conditions, is hydrolyzed uniformly to a nucleophilic group;

X is an acyclic, carbocyclic or heterocyclic linking group; and

E and NuP are joined to positions on X to form a 3- to 7-membered ring during the intramolecular nucleophilic displacement reaction between the electrophilic group and the nucleophilic group.

15. A photographic image transfer film unit of claim 14 wherein

PR-G' is the residue of a development inhibitor, a developing agent, an electron transfer agent, a bleach inhibitor or a nucleating agent.

16. A film unit of claim 15 further comprising an alkaline processing composition and means containing same for discharge of the alkaline processing composition within the film unit.

17. A film unit of claim 16 wherein the blocked photographic reagent is in or adjacent a silver halide emulsion layer.

18. A film unit of claim 16 further comprising a transparent cover sheet on the opposite side of the silver halide emulsion layers from the dye image receiving layer, and the means containing the alkaline processing composition being positioned for discharge of the alkaline processing composition between the cover sheet and the silver halide emulsion layers.

19. A film unit of claim 18 wherein the cover sheet comprises a transparent support bearing, in order, a neutralizing layer and a timing layer.

20. A photographic image transfer film unit of any one of claims 13 through 15 wherein the dye releasing compound is negative working.

21. A photographic image transfer film unit of any one of claims 13 through 15 wherein the dye releasing compound is positive working.

22. A photographic image transfer film unit of any one of claims 14 or 15 wherein the moiety -E-X-NuP has the structure $$\begin{array}{c} \overset{|}{\underset{\|}{C}}=O \\ R^1-N{+}CR_2{}^2{)_{\overline{n}}}O-\overset{O}{\overset{\|}{C}}R^3 \end{array}$$

$$\begin{array}{c} \overset{|}{\underset{\|}{C}}=O \\ R^1-N{+}CR_2{}^2{)_{\overline{n}}}N-\overset{O}{\overset{\|}{C}}R^3 \\ \phantom{R^1-N{+}CR_2{}^2{)_{\overline{n}}}}\overset{|}{R^4} \end{array}$$

or the structure:

$$\overset{|}{\underset{\|}{C}}{+}CH_2{)_{\overline{m}}}\overset{R^5}{\underset{R^5}{\overset{|}{C}}}{+}CR_2{}^2{)_{\overline{p}}}Y-\overset{O}{\overset{\|}{C}}R^3$$

wherein:

$R^1$ is hydrogen, straight or branch chain alkyl of 1 to 20 carbon atoms or aryl of 6 to 30 carbon atoms;

Each $R^2$ is individually hydrogen or alkyl of 1 to 6 carbon atoms;

$R^3$ is hydrogen, alkyl of 1 to 20 carbon atoms or aryl of 6 to 30 carbon atoms;

$R^4$ is $R^1$;

Y is —O—, —S—, or $$\overset{R^4}{\underset{}{\overset{|}{-N-}}};$$

Each $R^5$ is individually straight or branch chain alkyl of 1 to 6 carbon atoms;

n is 1 to 4;

m is 0 or 1;

p is 1 to 4; and m+p is 1 to 4.

23. A photographic image transfer film unit of any one of claims 14 or 15 wherein the moiety -E-X-NuP has the structure:

[structure with phenyl ring, $R^1-N$, $C=O$, $-CR_2{}^2{)_{\overline{q}}}O-\overset{O}{\overset{\|}{C}}-R^3$, $R^6$]

or the structure:

[structure with phenyl ring, $R^1-N$, $C=O$, $-(CR_2{}^2{)_{\overline{q}}}N-\overset{O}{\overset{\|}{C}}-R^3$, $R^4$, $R^6$]

or the structure:

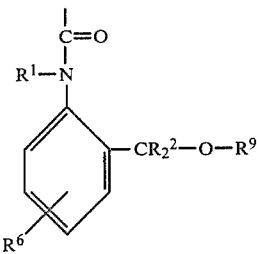

or the structure:

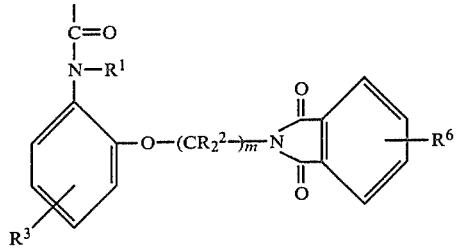

wherein:

R[1] is hydrogen, straight or branch chain alkyl of 1 to 20 carbon atoms or aryl of 6 to 30 carbon atoms;

Each R[2] is individually hydrogen or alkyl of 1 to 6 carbon atoms;

R[3] is hydrogen, alkyl of 1 to 20 carbon atoms or aryl of 6 to 30 carbon atoms;

R[4] is R[1];

q is 0 to 2;

R[6] is hydrogen, halogen, nitro, carboxy, straight or branch chain alkyl of 1 to 20 carbon atoms; alkoxy of 1 to 20 carbon atoms, aryl of 6 to 30 carbon atoms, alkoxycarbonyl of 2 to 20 carbon atoms; sulfamoyl having the structure —SO$_2$NR$^4{}_2$, sulfonamido having the structure —NR$^4$SO$_2$R$^4$, carbamoyl having the structure —CONR$^4{}_2$ or carbanamido having the structure —NR$^4$COR$^4$ where R[4] is R[1]; and R[9] is hydrogen, formyl or alkylcarbonyl.

24. A photographic image transfer film unit of any one of claims 14 or 15 wherein the moiety -E-X-NuP has the structure:

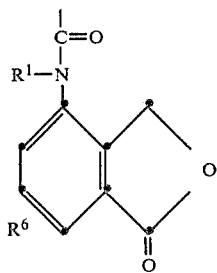

or the structure:

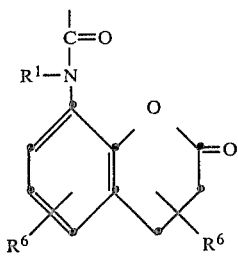

or the structure:

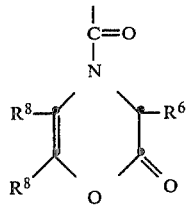

wherein:

R[1] is hydrogen, straight or branch chain alkyl of 1 to 20 carbon atoms or aryl of 6 to 30 carbon atoms;

R[6] is hydrogen, halogen, nitro, carboxy, straight or branch chain alkyl of 1 to 20 carbon atoms, alkoxy of 1 to 20 carbon atoms; aryl of 6 to 30 carbon atoms, alkoxycarbonyl of 2 to 20 carbon atoms; sulfamoyl having the structure —SO$_2$NR$^4{}_2$, sulfonamido having the structure —NR$^4$SO$_2$R$^4$, carbamoyl having the structure —CONR$^4{}_2$ or carbonamido having the structure —NR$^4$COR$^4$ where R[4] is R[1]; and each R[8] is R[6] or together both R[8]'s form a fused aromatic ring of 5 to 6 nuclear atoms selected from carbon, nitrogen, oxygen and sulfur, which ring can be optionally substituted with one or more R[6] groups.

25. A photographic image transfer film unit of any one of claims 14 or 15 wherein the moiety -E-X-NuP has the structure:

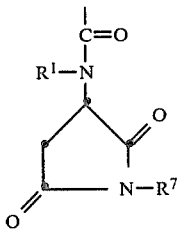

or the structure:

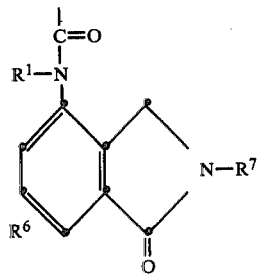

or the structure:

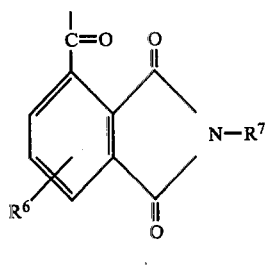

wherein:

R¹ is hydrogen, straight or branch chain alkyl of 1 to 20 carbon atoms or aryl of 6 to 30 carbon atoms;

R⁶ is hydrogen, halogen, nitro, carboxy, straight or branch chain alkyl of 1 to 20 carbon atoms; alkoxy of 1 to 20 carbon atoms, aryl of 6 to 30 carbon atoms, alkoxycarbonyl of 2 to 20 carbon atoms, sulfamoyl having the structure —SO₂NR⁴₂, sulfonamido having the structure —NR⁴SO₂R⁴, carbamoyl having the structure —CONR⁴₂ or carbonamido having the structure —NR⁴COR⁴ where R⁴ is R¹; and R⁷ is alkyl of 1 to 30 carbon atoms or aryl of 6 to 30 carbon atoms.

26. A photographic film unit of claim 15 wherein the blocked photographic reagent is a blocked developing agent selected from

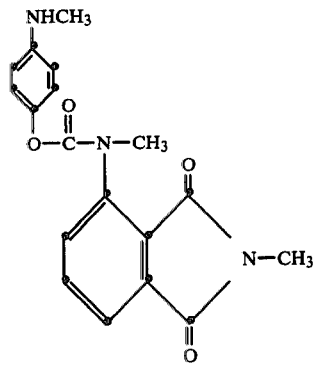

-continued

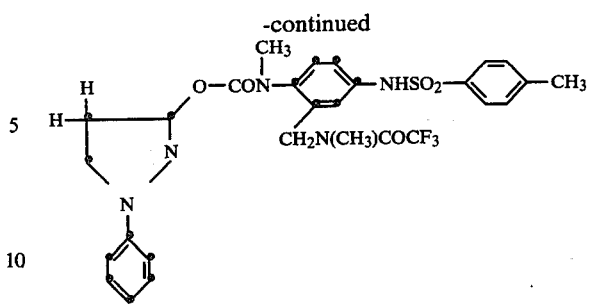

or the structure:

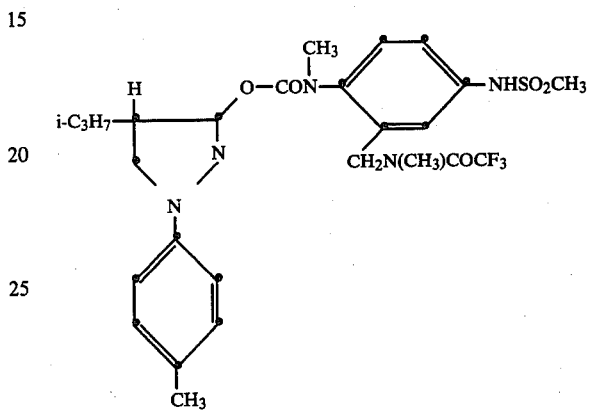

27. An image transfer dye image receiving element capable of being permeated by an alkaline processing composition, comprising a support having thereon a neutralizing layer, a timing layer and a dye image receiving layer, the element containing a blocked photographic reagent having the structure:

PR-G'-E-X-NuP where:

PR-G' is the residue of a photographic reagent, G' being oxygen, sulfur, selenium, phosphorous or nitrogen;

E is an electrophilic group;

NuP is a precursor of a nucleophilic group which, under alkaline conditions, is converted uniformly to a nucleophilic group; and X is a linking group for spatially relating E and NuP to enable them to undergo, after conversion of NuP to a nucleophilic group, an intramolecular nucleophilic displacement reaction which cleaves the bond between E and G';

the photographic reagent, under alkaline conditions encountered during processing of a silver halide emulsion layer, being uniformly unblocked, even if contacted with oxidized silver halide developing agent.

28. An image transfer dye image receiving element of claim 27 wherein

PR-G' is the residue of a development inhibitor, a developing agent, an electron transfer agent, a bleach inhibitor or a nucleating agent.

* * * * *

UNITED STATES PATENT AND TRADEMARK OFFICE
CERTIFICATE OF CORRECTION

PATENT NO. : 4,358,525
DATED : November 9, 1982
INVENTOR(S) : Jared B. Mooberry and William C. Archie, Jr.

It is certified that error appears in the above-identified patent and that said Letters Patent are hereby corrected as shown below:

Column 72, claim 8, line 60,

"
$$\begin{matrix} R^4 \\ | \\ -N- ; \end{matrix}$$
" should read -- Y is -O-, -S-, or $\begin{matrix} R^4 \\ | \\ -N- ; \end{matrix}$ --.

Column 73, claim 9, structure between lines 15-30,

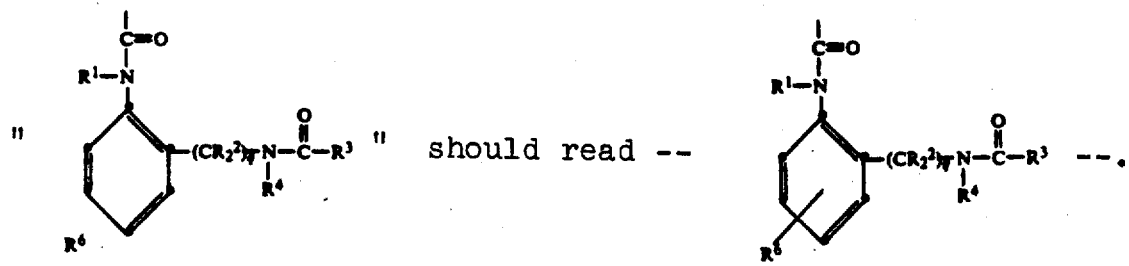

" should read --.

Column 78, claim 23, structure between lines 40-50,

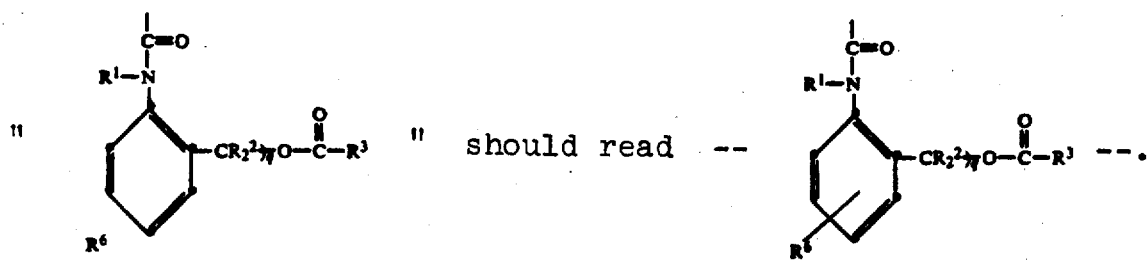

" should read --.

UNITED STATES PATENT AND TRADEMARK OFFICE
CERTIFICATE OF CORRECTION

PATENT NO. : 4,358,525
DATED : November 9, 1982
INVENTOR(S) : Jared B. Mooberry and William C. Archie, Jr.

It is certified that error appears in the above-identified patent and that said Letters Patent are hereby corrected as shown below:

Column 78, claim 23, structure between lines 55-65,

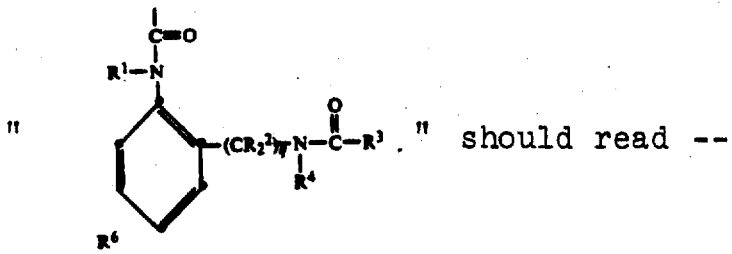

Column 79, claim 24, structure between lines 55-65,

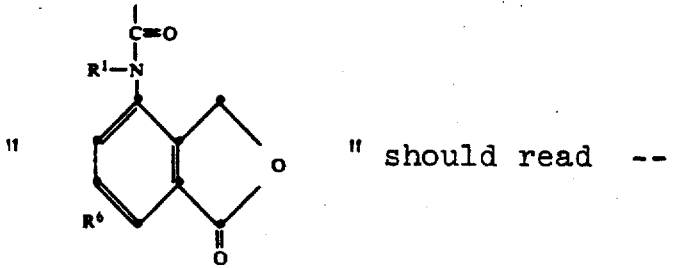

UNITED STATES PATENT AND TRADEMARK OFFICE
CERTIFICATE OF CORRECTION Page 3 of 3

PATENT NO. : 4,358,525
DATED : November 9, 1982
INVENTOR(S) : Jared B. Mooberry and William C. Archie, Jr.

It is certified that error appears in the above-identified patent and that said Letters Patent are hereby corrected as shown below:

Column 81, claim 25, structure between lines 1-15,

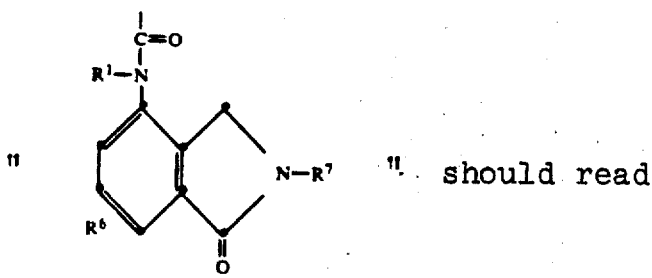 " should read -- 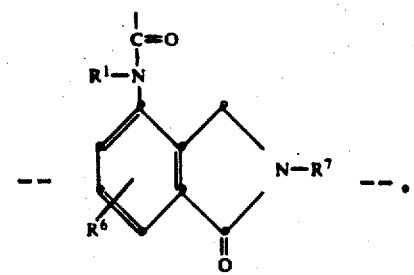 --.

Signed and Sealed this

Thirty-first Day of May 1983

[SEAL]

Attest:

DONALD J. QUIGG

Attesting Officer     Acting Commissioner of Patents and Trademarks